United States Patent
Deng

(12)
(10) Patent No.: US 6,667,295 B1
(45) Date of Patent: Dec. 23, 2003

(54) DNA VACCINE AGAINST FELINE IMMUNODEFICIENCY VIRUS

(75) Inventor: Ruitang Deng, Old Lyme, CT (US)

(73) Assignees: Pfizer, Inc., New York, NY (US); Pfizer Products, Inc., Groton, CT (US)

( * ) Notice: Subject to any disclaimer, the term of this patent is extended or adjusted under 35 U.S.C. 154(b) by 0 days.

(21) Appl. No.: 09/593,580

(22) Filed: Jun. 14, 2000

Related U.S. Application Data

(60) Provisional application No. 60/138,999, filed on Jun. 14, 1999.

(51) Int. Cl.[7] .................. A61K 31/7088; A61K 31/711; A61K 31/7105

(52) U.S. Cl. ...................... 514/44; 424/93.1; 424/93.2; 424/93.6; 424/278.1; 424/281.1; 424/188.1; 424/204.1; 424/208.1; 536/23.1; 536/23.72

(58) Field of Search .......................... 435/320.1, 235.1, 435/455, 456, 457, 325, 351; 424/93.1, 93.2, 93.6, 278.1, 281.1, 188.1, 204.1, 208.1; 536/23.1, 23.72

(56) References Cited

U.S. PATENT DOCUMENTS

| | | | | |
|---|---|---|---|---|
| 5,833,993 A | * | 11/1998 | Wardley et al. | 424/208.1 |
| 6,004,799 A | * | 12/1999 | Luciw et al. | 435/236 |
| 6,300,118 B1 | * | 10/2001 | Chavez et al. | 435/252.3 |
| 6,348,196 B1 | * | 2/2002 | Audonnet et al. | 424/202.1 |

FOREIGN PATENT DOCUMENTS

| | | |
|---|---|---|
| EP | 0997529 | 8/1999 |
| FR | 2751223 | 1/1998 |
| WO | WO9530019 | 11/1995 |
| WO | WO9640268 | 12/1996 |
| WO | WO9732983 | 9/1997 |
| WO | WO9803660 | 1/1998 |
| WO | WO9821354 | 5/1998 |
| WO | WO9840493 | 9/1998 |
| WO | WO9840957 | 9/1998 |

OTHER PUBLICATIONS

M. J. Hoesie, et al., DNA Vaccination Affords Significant Protection Against Feline Immunodeficiency Virus Infection without Inducing Detectable Antiviral Antibodies, Journal of Virology, New York, US, vol. 72, No. 9, Sep. 1998, pp. 7310–7319.

A. M. Cuisinier, et al., Attempt to Modify the Immune Response Developed Against FIV gp120 Protein by Preliminary FIV DNA Injection, Vaccine, GB, Butterworth Scientific. Guildford, vol. 17, No. 5, Feb. 1999, pp. 415–425.

J. D. Boyer, et al., Protection of Chimpanzees from High–does Heterrologous HIV–1 Challenge by DNA Vaccination, Nature Medicine, vol. 3, No. 5, 1997, pp. 526–532.

V. Schwedler UTA, et al., Retroviral–Medicated Expression of FIV Envelope/Rev Induces CD8+CTL Responses In Mice., Intervirology, vol. 40, No. 4, Jul. 1997, pp. 271–276.

Olmsted et al. Molecular cloning of feline immunodeficiency virus. Proc. Natl. Acad. Sci. USA. Apr. 1989, vol. 86, pp. 2448–2452. See entire document.

Whetter et al. Equine infectious anemia virus derived from a molecular clone persistently infects horses. J. Virol. Dec. 1990, vol. 64, No. 12, pp. 5750–5756. See entire document.

Andresson et al. Nucleotide sequence and biological properties of a pathogenic proviral molecular clone of neurovirulent visna virus. Virol. 1993, vol. 193, pp. 89–105. See entire document.

Saltarelli et al. Nucleotide sequence and transcriptional analysis of molecular clones of CAEV which generate infectious virus. Virol. 1990, vol. 179, pp. 347–364. See entire document.

Franchini et al. Highly attenuated HIV type 2 recombinanat poxviruses, but not HIV–2 recombinant Salmonella vaccines, induce long–lasting protection in rehsus macaques. AIDS Res. Human Retro. 1995, vol. 11, No. 8, pp. 909–920. See entire document.

Cox et al. Induction of cytotoxic T lymphocytes by recombinant canarypox (ALVAC) and attenuated vaccinia (NYVAC) viruses expressing the HIV–1 envelope glycoprotein. Virol. 1993, vol. 195, pp. 845–850. See entire document.

Wardley et al. The use of feline herpesvirus and baculovirus as vaccine vectors for the gag and env genes of feline leukaemia virus. J. Gen. Virol. 1992, vol. 73, pp. 1811–1818. See entire document.

Pincus et al. Poxvirus–based vectors as vaccine candidates. Biologicals. 1995, vol. 23, pp. 159–164. See entire document.

Okuda et al. Induction of potent humoral and cell–mediated immune responses following direct injection of DNA encoding the HIV type 1 env and rev gene products. AIDS Res. Human Retro. 1995, vol. 11, No. 8, pp. 933–943. See entire document.

Gonda et al. Bovine immunodeficiency virus: molecular biology and virus–host interactions. Virus Res. 1994, vol. 32, pp. 155–181. See entire document.

Baldinotti et al., 1994, J. Virol., vol. 68:4572–5479.
Bishop et al., 1996, Vaccine, vol. 14:1243–1250.
Baumberger et al., 1993, AIDS, 7:S59–S64.
Cuisinier et al., 1997, Vaccine, vol. 15:1085–1094.
Diehl et al., 1995, J. Virol., vol. 69:2328–2332.
Diehl et al., 1996, J. Virol. vol. 70:2503–2507.
Elyar et al., 1997, Vaccine, vol. 15:1437–1444.

(List continued on next page.)

Primary Examiner—David Guzo
(74) Attorney, Agent, or Firm—Paul H. Ginsburg; Lorraine B. Ling; Kohn & Associates, PLLC

(57) ABSTRACT

The present invention is directed to vaccine compositions that can be used to protect cats against feline immunodeficiency virus. More particularly, the present invention relates to polynucleotide molecules that can be used as vaccine components against feline immunodeficiency virus.

2 Claims, 7 Drawing Sheets

OTHER PUBLICATIONS

Figure 1:
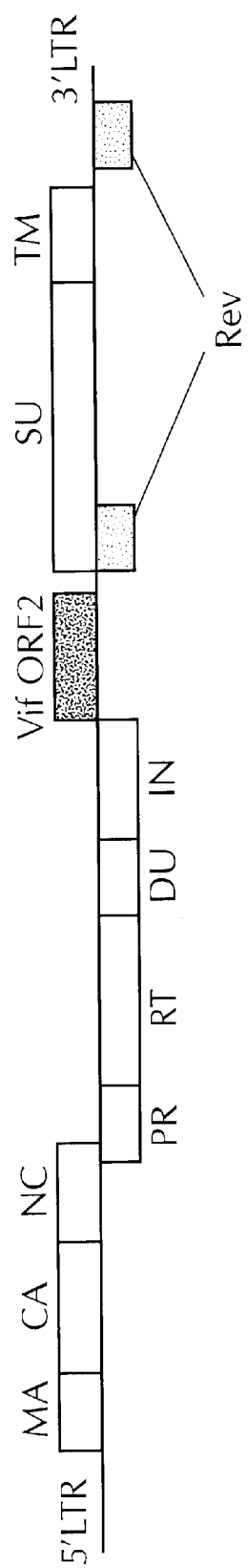

English et al, 1994, J. Infect. Disc., vol. 170:543–552.
Flynn et al., 1997, J. Virol, vol. 71:7586–7592.
Flynn et al., 1996, J. Immunol., vol. 157:3658–3665.
Flynn et al., 1995, AIDS Res. Hum. Retrovir., vol. 11:1107–1113.
Flynn et al., 1995, Immunol., vol. 85:171–175.
Gonin et al., 1995, Vet. Microbiol, vol.: 45:393–401.
Graziosi et al., 1993, Proc. Nat'l Acad. Sci., vol. 90:6405–6409.
Hohdatsu et al., 1993, J. Virol., vol. 67:2344–2348.
Hosie et al., 1995, J. Virol., vol. 69:1253–1255.
Hosie and Flynn, 1996, J. Virol., vol. 70:7561–7568.
Hosie et al., 1992, Vet. Immunol. Immunopathol., vol. 35:191–197.
Huisman et al., 1998, Vaccine, vol. 16:181–187.
Ishida and Tomoda, 1990, JPN. J. Vet. Sci., vol. 52:645–648.
Kakinuma et al., 1995, J. Virol., vol. 69:3639–3646.
Lombardi et al., 1994, J. Virol, Vol 68:8374–8379.
Lutz et al., 1995, Vet. Immunol. Immunopathol., vol. 46:103–113.
Mascola et al, 1993, AIDS Res. Hum. Retrovir, vol. 9:1175–1184.
Matteucci et al., 1997, J. Virol., vol. 71:8368–8376.
Matteucci et al., 1996, J. Virol., vol. 70:617–622.
Olmsted et al., 1989, Proc. Nat'l Acad. Sci. USA, vol., 86:8088–8092.
Osterhaus et al., 1996, AIDS Res. Hum. Retrovior, vol., 12:437–441.
Pecoraro et al., 1996, J. Gen. Virol., vol. 77:2031–2035.
Pu et al., 1995, AIDS, vol. 9:235–242.
Rigby et al., 1996, Vaccine, vol. 14:1095–1102.
Siebelink et al., 1995, J. Virol., vol. 69:3704–3711.
Sodora et al., 1994, J. Virol., vol. 68:2230–2238.
Talbott et al., 1989, Proc. Nat'l Acad. Sci. USA, vol. 86:5743–5747.
Tijhaar et al., 1997, Vaccine, vol. 15:587–596.
Verschoor et al., Vaccine, vol. 14:285–289.
Verschoor et al., 1995, Vet. Immunol Immunopathol., vol., 46:139–149.
Wei et al., 1995, Nature, vol. 373:117–122.

* cited by examiner

SEQUENCE LISTING

<160> NUMBER OF SEQ ID NOS: 52

<210> SEQ ID NO 1
<211> LENGTH: 9464
<212> TYPE: DNA
<213> ORGANISM: Feline immunodeficiency virus

<400> SEQUENCE: 1

```
tgggaagatt attgggatcc tgaagaaata gaaaaaatgc taatggactg aggacgtaca      60
taaacaagtg acagatggaa acagctgaat atgactcaat gctagcagct gcttaaccgc     120
aaaaccacat cctatgtaaa gcttgccgat gacgtgtatc ttgctccatt ataagagtat     180
ataaccagtg ttttgtaaaa gcttcgagga gtctctctgt tgagggcttt cgagttctcc     240
cttgaggctc ccacagatac aataaaaaac tgagctttga gattgaaccc tgtcttgtat     300
ctgtgtaatt tctcttacct gcgaatccct ggagtccggg ccagggacct cgcagttggc     360
gcccgaacag ggacttgaaa aggagtgatt agggaagtga agctagagca atagaaagct     420
gtcaagcaga actcctgcag gccttgtatg gggagcagtt gcagacgctg ctggcagtga     480
gtatctctag tggagcggac ctgagctctg gattaagtca ctgctcacag gcctagataa     540
agattatctg gtgactcttc gcggatcgtc aaaccagggg attcgtcggg ggacagccaa     600
caaggtagga gagattctac agcaacatgg ggaatggaca ggggcgagac tggaaaatgg     660
ccattaagag atgtagtaat gttgctgtag gggtagggag caggagtaaa aaatttggag     720
aaggaaattt tagatgggcc ataaggatgg ctaatgtaac tacaggacga gaacctggtg     780
atataccaga gactttagaa cagctaagat caatcatttg tgacttacaa gacagaagag     840
aacaatatgg atctagtaaa gaaattgaca tggcaattac cactttaaaa gttttttgcag     900 tggcaggaat tctaaatatg actgtaacta ctgccacagc agctgaaaat atgtatgctc     960
```

```
agatgggatt agacaccaga ccatctataa aagaaagtgg gggaaaagaa gaaggacctc   1020
cacaggctta tcctattcaa acagtaaatg gagcaccaca gtatgtagcc cttgatccaa   1080
aaatggtgtc tatttttatg gagaaggcaa gagagggct aggaggtgaa gaagtccaac    1140
tgtggtttac agccttttca gctaatttaa catcaactga tatggctaca ttaattatgt   1200
ccgcacctgg ctgtgcagca gataaagaaa tcctagatga aacactgaaa cagatgacag   1260
ctgagtatga tcgtacccat cctcctgatg ggcctagacc gctgccctat ttcactgccg   1320
cagagatcat gggatagga ttgactcaag aacaacaagc agaacccagg tttgccccag    1380
ccagaatgca gtgtagagca tggtatcttg aagcattagg aaagctagcg gccataaaag   1440
ccaaatctcc ccgagcagta caattgaagc agggagctaa agaggactat tcctcattca   1500
tagatagact atttgctcaa atagatcaag agcagaacac agctgaggta aagctgtatt   1560
taaaacaatc tttgagcata gcaaatgcta atccagattg taagagagcg atgagtcatc   1620
ttaaaccaga aagtacttta gaagagaaac tgagagcctg ccaggaaata ggatcgccag   1680
gatacaaaat gcaactattg gcagaggctc ttactagggt gcaaacagtt caagcaaaag   1740
gaccaaggcc agtatgtttc aattgtaaaa aaccaggaca cctggccaga caatgtagac   1800
aagcaaagag atgtaataaa tgtggaaaac ctggtcactt agctgctaac tgttggcaag   1860
gaggtaaaaa gtccccggga acggggcga tggggcgagc tgcagcccca gtaaatcaag    1920
tgcagcaagt gataccatct gcaccccccgg tagaggagaa attgttagat atgtaaacta   1980
taataaagtg ggtaccacca caactttaga aaaagacct gaaatacaaa tattcgtaaa    2040
tgggtatcct ataaaatttt tattagatac aggagcagat ataacaattt taaacagaaa   2100
agactttcag atagggaatt ctatagaaaa tgggaaacag aatatgattg gagtaggagg   2160
cggaaagaga ggaacaaatt atatcaatgt gcatttagaa attagagatg aaaattataa   2220
gacacagtgt atatttggaa atgtgtgtgt cttggaggat aattcattaa tacaaccatt   2280
attgggaaga gataacatga ttaagttcaa cataaggttg gtaatggctc aaatttcaga   2340
gaaaattcca atagtaaaag taagaatgaa agaccctact caagggcctc aggtaaaaca   2400
atggccatta tcaaatgaga aaattgaagc tctaactgac atagtaaaca ggttagaaca   2460
agagggaaag gtaaaaagag ctgatccaaa taatccttgg aacactcccg tatttgcaat   2520
caagaaaaag aatggtaaat ggagaatgct catagatttt aggtcctaa ataaattaac    2580 agacaaaggg gcagaagttc agttaggact ccctcatcct gctggattac aattgaaaaa   2640
acaagtaact gtattggaca taggggacgc atatttttact attcctctag atccagatta   2700
tgctccttat actgcattta cactacctag aaaaaacaat gcaggaccag ggaggagata   2760
catatggtgt agtttaccac aagggtgggt cttgagtcca ttgatatatc agagtacctt   2820
agacaatata ctccaacctt ttattaaaca gaatcctgag ttagatattt atcaatatat   2880
ggatgatatc tataggat caaatttaag taaaaggaa cataaactaa agtagaaga      2940 attaagaaaa ttgttattat ggtggggatt tgaaccccg gaagataaat tacaagaaga    3000 gccccctat aagtggatgg gctatgaatt acatccatta acgtggtcaa tacagcaaaa    3060
gcaattagaa attccagaga gacccacatt aaatgaatta cagaagttag caggtaagat   3120
taactgggct agtcaaacca ttccagactt gagcataaaa gaactaacta atatgatgag   3180
aggagatcaa aagttagact caataagaga atggacgaca gaggccaaga tgaagtgga   3240 gaaagctaag agagcaattg agacacaggc acagctagga tattatgatc ctaatcgaga   3300
```

```
attatatgct aaattaagtc ttgtgggacc acatcaacta agctatcagg tgtatcataa    3360
aaacccagaa cagatattat ggtatgggaa aatgaatagg cagaagaaaa aagcagaaaa    3420
tacttgtgat atagctctaa gggcatgtta caaaataaga aagaatcca ttataagaat    3480
aggaaaagaa ccagtatatg aaatacctac atccagagaa gcttgggaat caaatctaat    3540
tagatctcca tatcttaagg cctcaccacc tgaggtggaa tttatacatg ctgccttaaa    3600
tataaaaaga gctctaagca tgatacaaga tgcccctata ttgggagcag aaacatggta    3660
catagatggg ggaagaaaac aaggaaaagc agcaagagca gcttattgga cagatacggg    3720
cagatggcag gtaatggaaa tagaaggaag taatcaaaaa gcagaagtac aagctttatt    3780
attggcccta caggcaggac cagaggaaat gaatattata acagattcac aatatattgt    3840
gaatattatt aatcaacaac cagatttgat ggaaggaatt tggcaagaag tcttagaaga    3900
aatggaaaag aaagtagcaa tctttataga ttgggtacct ggacataaag gtattccagg    3960
aaataaagag gtagatgaac tttgtcaaac gatgatggtt atagaaggtg aaggaatatt    4020
agataaaaga tcagaagatg caggatatga tttattagct gcacaagaaa tacatctctt    4080
gcctggggag gtaagagtag taccaacaag aacaaagata atgttaccta aaggatattg    4140
gggattaata atgggaaaaa gttcaatggg aagcaaagga ttagatgtat taggaggagt    4200
tatagatgaa ggatatagag gagaattagg ggtgataatg attaacctat ctaaaaaatc    4260
aataacatta tcagaaaaac aaaaagtagc acaattaata atattccctt gtaaacatga    4320
aagcttacaa caaggagaaa taataatgga ttcagaaaga ggaagaaagg gatttgggtc    4380
aactggagtc ttttcttcat gggtggacag aattgaggaa gcagaattaa atcatgaaaa    4440
atttcactca gacccacaat acttaagaac agaatttaat ctacccagaa tagtagcaga    4500
ggaaataaaa agaaaatgtc ccttatgtag aatcagaggg gaacaagtag ggggacaatt    4560
aaagattgga cctggcatat ggcaaatgga ctgtacacac tttaatggaa aaataattat    4620
tgtcgcagtg catgtggaat caggcttatt atgggcacag gtaattccac aggagactgc    4680
agattgtaca gttaaagctc tcatgcaact tatcagtgct cataatgtta cagaactaca    4740
aacagataat ggaccaaatt ttaaaaatca gaaatggaa ggactactaa attatatggg    4800
cataaaacac aaattaggta taccaggtaa cccacaatca caagcattag tagaaaatgc    4860
taaccacaca ttaaaatctt ggattcaaaa atttctctca gaaacttctt ctttggacaa    4920
cgcattggcc ctagccttat actgcctcaa ttttaaacaa aggggtagac tagggagaat    4980
ggctccttat gaattataca tacaacagga atcattaaga atacaagact atttttcaca    5040
aattccacaa aaattaatga tgcaatgggt gtattataaa gatcagaaag ataaaaagtg    5100
gaagggacca atgagagtag aatattgggg acaaggatca gtattattaa agaatgaaga    5160
gaagggatat tttcttgtac ctaggagaca cataagaaga gtcccagaac cctgcactct    5220
tcctgaaggg gatgagtgac gaagattggc aggtaagtag aagactcttt gcagttctcc    5280
aaggaggagt aaatagtgcc atgttataca tatcgaattt acctgaaaca gaacaggcac    5340
aatataaaaa ggactttaag aaaaggctct tagaaaagga gactggattc atctatagat    5400
taagaaaagc tgaaggaata aggtggagct ttcatacgcg tgattattat ataggatatg    5460
taagagagat ggtggctggg tctagcctac aaaatagttt aagattgtat gtttatataa    5520
gcaatccatt gtggcatcag tcataccgtc ctggcctgac aaatttttaat acagagtggc    5580
cttttgtaaa tatgtggata aagacaggat ttatgtggga tgatattgaa agccaaaata    5640
tttgcaaagg aggagagatc tcacatggat ggggacctgg aatggtggga attgtgataa    5700
```

```
aagcatttag ctgtggagaa aggaagatac aaattactcc tgtcatgatt ataagaggtg      5760
agatagaccc acagaaatgg tgtggagatt gttggaatct gatgtgtctt aaatattcac      5820
ttccaaatac attgcagagg cttgctatgc tggcgtgtgg caaagaggct aaagaatgga      5880
gaggctgttg taatcagcgt tttgtttctc ctttcagaac accctgtgat ctagaggtcg      5940
tccagaacaa gcctaaaagg aatttattgt ggacgggaga attatgaatg gaagaaataa      6000
tcccactgtt taataaggtt acagaaaagt tagatagaga agcagctatt agattgttta      6060
ttttagctta tcaggtagac agatgcagat ttattagaat tttacaatta ttactttgga      6120
gagatagatt taagtcaatc aattctaaat attgtttatg ctggctgtgc tgcaagtctg      6180
cttattggcg cttgcaatct acattatcca taaatactgc ctagaaatat ttcttttaat      6240
atttcatctg cagatataaa catggcagag ggaggattta ctcaaaatca acaatggata      6300
gggccagaag aagctgaaga attgttagat tttgatatag ctgtacaaat gaatgaagaa      6360
ggtccattaa acccaggagt aaacccattt agggtaccag gaattacctc tcaagaaaag      6420
gatgattatt gtcagatttt acaaccaaaa ctacaagaat aaagaatga aatcaaagag       6480 gtaaaacttg acgaaaacaa tgcaggtaag tttagaaagg caagatattt aagatattct      6540
gatgagagtg tactaactat agtctatttta ctaacaggat atttgagata tttaataagc      6600
catagaaact taggatcttt aagacatgat atagatatag aagcaccaca acaagagcac      6660
tataatgata aagaaaaggg tactacttta aatataaagt atgggagaag atgttgtatt      6720
agcacattac ttctatattt aatcctcttc tcagggatag gaatttggct tggaaccaaa      6780
gcacaagtag tgtggagact ccctccttta gtagtgccag tagatgagac agaaataata      6840
ttttgggatt gttgggcgcc agaggaacca gcctgtcaag atttttctggg aacaatgata     6900 catttaaaag caaatgttaa tataagtata caagaaggac ctacattggg aaattgggca     6960
agggaaattt ggtctacatt atttaaaaaa gctacaaggc aatgcagaag gggaaggata     7020
tggaagaaat ggaatgagac tataacagga cctaaaggat gtgcaaataa tacctgttat     7080
aatatttcag tagtggtacc tgattatcaa tgttatgtag acagagtaga tacatggctg     7140
caaggaaaag ttaatatctc actatgtttg acaggaggaa agatgctata taataaaaat     7200
acaaaacaat taagttactg tacagatcca ttacaaatac cattaattaa ttacacattt     7260
ggacctaacc aaacttgtat gtggaacaca tctttaatca aagaccctga gataccgaaa     7320
tgtggatggt ggaaccaggc agcctattat aataattgta aatgggaaga agctaatgtg     7380
acatttcaat gtcaaagatc acaaagtcta ccaggatcat gggttaggag aatctcttca     7440
tggagacaaa gaaacagatg ggagtggagg ccagactttg aaagtgagaa agtaaaaata     7500
tcattacaat gtaatagtac aaaaaattta actttttgcaa tgagaagttc aagtgattat     7560
tatgatgtac aaggagcatg gatagaattt ggatgttata gaaataaatc aagaaccat     7620 acgggagcaa gatttagaat aagatgtaaa tggaatgaag gaagaatct atctctcatt      7680 gatacatgtg ggactacttc aaatgtgaca ggagccaacc ctgtagattg tactatgaaa     7740
acaagcacta tgtacaattg ttccttacaa gatagtttca ctatgaaaat agaggacctt     7800
attgtacaat ttaatatgac aaaagcagtg gaaatgtata atattgctgg gaattggtct     7860
tgtacatctg atttaccaac agggtgggga tatatgaaat gtaattgtac aaatgccact     7920
gatgggagga taaaatgaa atgccctagg aatcagggta ttttaagaaa ctggtacaat     7980
ccagttgcag gactaagaca agctcttatg aagtatcaag tagtaaaaca accagaatat     8040
```

-continued

```
ttggtggtac cggaagaagt tatgaggtat aaaggtaaac aaaaaagggc cgctattcat    8100
attatgttag cccttgctac ggtgttatct atagctggag caggaaccgg tgccactgct    8160
attgggatgg tgacacacta tcagcaagtt ttggctaccc atcagcaggc attggacaaa    8220
ataactgagg cactgaaaat aaacaactta aggttaatca ctttagaaca tcaagtatta    8280
gtgatagggt taaagtaga ggctatagaa aaattcctat atacagcttt tgctatgcaa     8340
gaattaggat gtaatcagaa tcaattcttt tgtaagattc ccctcaatct gtggacaatg    8400
tataacatga ctataaatca tacactatgg aatcatggaa atataacttt gggagaatgg    8460
tataatcaaa caaaagtttt acaagaaaaa ttttatgaga taattatgga tatagaacaa    8520
aataatgtac aagggaaaaa tggaatacaa caattacaaa aatgggaaaa ttgggtggga    8580
tggataggca aaatccctca atatttaaaa ggacttcttg gtagtgtgtt gggaatagga    8640
ctaggaatct tactactact tatatgcttg cctacattag tagattgtat aagaaactgt    8700
actaataaaa tattgggata tacagttatt gcaatgcctg aaatagatga tgaggaagta    8760
cacccatcag tggaattgag gagaaatggc aggcaatgtg gcatatctga aaagaggag    8820 gaatgatgga gcatttcaga cctgtagaat acaggagtaa tgctgagctg agttcttccc    8880
tttgaggagg atgtgtcata tgaatccatt tcaaatcaaa aataacagta aaatctatat    8940
tgtaaggcaa acgaaaaaga caacgcagaa gaagaaagaa gaaggccttc aaaaaattga    9000
tgctggattt agaggctcga tttaaagcgt tgtttgaaac accttcagct acagaatata    9060
ctgcagacga gacagaagaa gagactcttg aaaaagaaaa aagggtggac tgggaagatt    9120
attgggatcc tgaagaaata gaaaaaatgc taatggactg aggacgtaca taaacaagtg    9180
acagatggaa acagctgaat atgactcaat gctagcagct gcttaaccgc aaaaccacat    9240
cctatgtaaa gcttgccgat gacgtgtatc ttgctccatt ataagagtat ataaccagtg    9300
ttttgtaaaa gcttcgagga gtctctctgt tgagggcttt cgagttctcc cttgaggctc    9360
ccacagatac aataaaaaac tgagctttga gattgaaccc tgtcttgtat ctgtgtaatt    9420
tctcttacct gcgaatccct ggagtccggg ccagggacct cgca                    9464
```

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: PRIMER

<400> SEQUENCE: 2
ccgcaaaacc acatcctatg taaagcttgc                                      30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: PRIMER

<400> SEQUENCE: 3
cgcccctgtc cattccccat gttgctgtag                                      30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: PRIMER

<400> SEQUENCE: 4
acaaacagat aatggaccaa attttaaaaa					30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: PRIMER

<400> SEQUENCE: 5
gcaatgtggc atgtctgaaa aagaggagga					30

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: PRIMER

<400> SEQUENCE: 6
tctgtgggag cctcaaggga gaactc					26

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: PRIMER

<400> SEQUENCE: 7
tcttcccttt gaggaagata tgtcatatga atcc					34

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: PRIMER

<400> SEQUENCE: 8
ttactgtttg aataggatat gcctgtggag					30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: PRIMER

<400> SEQUENCE: 9
ttaaaggatg aagagaaggg atattttctt					30

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: PRIMER

<400> SEQUENCE: 10
tttcaatatc atcccacata aatcctgt					28

<210> SEQ ID NO 11

```
<211> LENGTH: 30
<212> TYPE: DNA
<213> ORGANISM: Artificial Sequence
<220> FEATURE:
<223> OTHER INFORMATION: Description of Artificial Sequence: PRIMER

<400> SEQUENCE: 11
tgggaagatt attgggatcc tgaagaaata                                    30

<210> SEQ ID NO 12
<211> LENGTH: 40
<212> TYPE: DNA
<213> ORGANISM: Artificial Sequence
<220> FEATURE:
<223> OTHER INFORMATION: Description of Artificial Sequence: PRIMER

<400> SEQUENCE: 12
catatcctat ataataatca cgcgtatgaa agctccacct                         40

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: PRIMER

<400> SEQUENCE: 13
aggtggagct ttcatacgcg tgattattat ataggatatg                         40

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: PRIMER

<400> SEQUENCE: 14
tgcgaggtcc ctggcccgga ctcc                                          24

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: PRIMER

<400> SEQUENCE: 15
ctccagggat tcgcaggtaa gagaaatta                                     29

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: PRIMER

<400> SEQUENCE: 16
tttcatctgc atcgataaac atggcggagg gagg                               34

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: PRIMER

<400> SEQUENCE: 17
```
cctgtattct actagtctga aatgctccat cat                                    33

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: PRIMER

<400> SEQUENCE: 18
tttcatctgc atcgataaac atggcggagg gagg                                   34

<210> SEQ ID NO 19
<211> LENGTH: 49
<212> TYPE: DNA
<213> ORGANISM: Artificial Sequence
<220> FEATURE:
<223> OTHER INFORMATION: Description of Artificial Sequence: PRIMER

<400> SEQUENCE: 19
gggctaacat aatatgacta gttcaccttt tttgtttacc tttatacct                   49

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: PRIMER

<400> SEQUENCE: 20
ggtaggatcg attctacagc aacatgggga atgg                                   34

<210> SEQ ID NO 21
<211> LENGTH: 42
<212> TYPE: DNA
<213> ORGANISM: Artificial Sequence
<220> FEATURE:
<223> OTHER INFORMATION: Description of Artificial Sequence: PRIMER

<400> SEQUENCE: 21
gtcttcacta gtaagttgtg gtagtaccca ttgtattata gt                          42

<210> SEQ ID NO 22
<211> LENGTH: 38
<212> TYPE: DNA
<213> ORGANISM: Artificial Sequence
<220> FEATURE:
<223> OTHER INFORMATION: Description of Artificial Sequence: PRIMER

<400> SEQUENCE: 22
ggtaaaaatc gatcatgaaa cggggcgatg gggcgagc                               38

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence: PRIMER

<400> SEQUENCE: 23
actgcaacta gtcttctact tacctgccaa tcttcg                                 36

<210> SEQ ID NO 24
<211> LENGTH: 37
<212> TYPE: DNA

```
<213> ORGANISM: Artificial Sequence
<220> FEATURE:
<223> OTHER INFORMATION: Description of Artificial Sequence: PRIMER

<400> SEQUENCE: 24
tgttagatcg ataatgtata ataaagtggg taccacc                            37

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: PRIMER

<400> SEQUENCE: 25
actgcaacta gtcttctact tacctgccaa tcttcg                             36

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence: PRIMER

<400> SEQUENCE: 26
ggtaggatcg attctacagc aacatgggga atgg                               34

<210> SEQ ID NO 27
<211> LENGTH: 37
<212> TYPE: DNA
<213> ORGANISM: Artificial Sequence
<220> FEATURE:
<223> OTHER INFORMATION: Description of Artificial Sequence: PRIMER

<400> SEQUENCE: 27
ctgtttgggg cccataagcc tgtggaggtc cttcttc                            37

<210> SEQ ID NO 28
<211> LENGTH: 44
<212> TYPE: DNA
<213> ORGANISM: Artificial Sequence
<220> FEATURE:
<223> OTHER INFORMATION: Description of Artificial Sequence: PRIMER

<400> SEQUENCE: 28
ggacctatcg ataccatgcc tattcaaaca gtaaatggag cacc                    44

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: PRIMER

<400> SEQUENCE: 29
tgcttggggc ccttgcaccc tagtaagagc ctctgc                             36

<210> SEQ ID NO 30
<211> LENGTH: 42
<212> TYPE: DNA
<213> ORGANISM: Artificial Sequence
<220> FEATURE:
<223> OTHER INFORMATION: Description of Artificial Sequence: PRIMER

<400> SEQUENCE: 30
ggctcttatc gataccatga cagttcaagc aaaaggacca ag                      42
```

<210> SEQ ID NO 31
<211> LENGTH: 38
<212> TYPE: DNA
<213> ORGANISM: Artificial Sequence
<220> FEATURE:
<223> OTHER INFORMATION: Description of Artificial Sequence: PRIMER

<400> SEQUENCE: 31
tattatgggc cccatatcta acaatttctc ctctaccg                               38

<210> SEQ ID NO 32
<211> LENGTH: 44
<212> TYPE: DNA
<213> ORGANISM: Artificial Sequence
<220> FEATURE:
<223> OTHER INFORMATION: Description of Artificial Sequence: PRIMER

<400> SEQUENCE: 32
ccctgcactc ttcatcgata ccatgagtga cgaagattgg cagg                        44

<210> SEQ ID NO 33
<211> LENGTH: 47
<212> TYPE: DNA
<213> ORGANISM: Artificial Sequence
<220> FEATURE:
<223> OTHER INFORMATION: Description of Artificial Sequence: PRIMER

<400> SEQUENCE: 33
gggattattt cttcgggccc taattctcct gtccacaata aattcct                     47

<210> SEQ ID NO 34
<211> LENGTH: 42
<212> TYPE: DNA
<213> ORGANISM: Artificial Sequence
<220> FEATURE:
<223> OTHER INFORMATION: Description of Artificial Sequence: PRIMER

<400> SEQUENCE: 34
ttgtggacgg gaatcgatac catggaagaa ataatcccac tg                          42

<210> SEQ ID NO 35
<211> LENGTH: 42
<212> TYPE: DNA
<213> ORGANISM: Artificial Sequence
<220> FEATURE:
<223> OTHER INFORMATION: Description of Artificial Sequence: PRIMER

<400> SEQUENCE: 35
atattaaaag aaatagggcc cggcagtatt tatggataat gt                          42

<210> SEQ ID NO 36
<211> LENGTH: 46
<212> TYPE: DNA
<213> ORGANISM: Artificial Sequence
<220> FEATURE:
<223> OTHER INFORMATION: Description of Artificial Sequence: PRIMER

<400> SEQUENCE: 36
gtataaaggt atcgatacca tggccgctat tcatattatg ttagcc                      46

<210> SEQ ID NO 37
<211> LENGTH: 42
<212> TYPE: DNA
<213> ORGANISM: Artificial Sequence
<220> FEATURE:

<223> OTHER INFORMATION: Description of Artificial Sequence: PRIMER

<400> SEQUENCE: 37
tgaaatgctg ggcccttcct cctcttttttc agatatgcca ca                    42

<210> SEQ ID NO 38
<211> LENGTH: 34
<212> TYPE: DNA
<213> ORGANISM: Artificial Sequence
<220> FEATURE:
<223> OTHER INFORMATION: Description of Artificial Sequence: PRIMER

<400> SEQUENCE: 38
tttcatctgc atcgataaac atggcggagg gagg                              34

<210> SEQ ID NO 39
<211> LENGTH: 36
<212> TYPE: DNA
<213> ORGANISM: Artificial Sequence
<220> FEATURE:
<223> OTHER INFORMATION: Description of Artificial Sequence: PRIMER

<400> SEQUENCE: 39
tgtacggggc ccgtccatta gcatttttc tatttc                             36

<210> SEQ ID NO 40
<211> LENGTH: 37
<212> TYPE: DNA
<213> ORGANISM: Artificial Sequence
<220> FEATURE:
<223> OTHER INFORMATION: Description of Artificial Sequence: PRIMER

<400> SEQUENCE: 40
tgttagatcg ataatgtata ataaagtggg taccacc                           37

<210> SEQ ID NO 41
<211> LENGTH: 43
<212> TYPE: DNA
<213> ORGANISM: Artificial Sequence
<220> FEATURE:
<223> OTHER INFORMATION: Description of Artificial Sequence: PRIMER

<400> SEQUENCE: 41
ctctgaaacg ggccccatta ccaaccttat gttgaactta atc                    43

<210> SEQ ID NO 42
<211> LENGTH: 46
<212> TYPE: DNA
<213> ORGANISM: Artificial Sequence
<220> FEATURE:
<223> OTHER INFORMATION: Description of Artificial Sequence: PRIMER

<400> SEQUENCE: 42
aacataatcg ataccatggt ccagatttca gagaaaattc caatag                 46

<210> SEQ ID NO 43
<211> LENGTH: 39
<212> TYPE: DNA
<213> ORGANISM: Artificial Sequence
<220> FEATURE:
<223> OTHER INFORMATION: Description of Artificial Sequence: PRIMER

<400> SEQUENCE: 43
ttctaggggc cccatcgttt gacaaagttc atctacctc                         39

<210> SEQ ID NO 44
<211> LENGTH: 43
<212> TYPE: DNA
<213> ORGANISM: Artificial Sequence
<220> FEATURE:
<223> OTHER INFORMATION: Description of Artificial Sequence: PRIMER

<400> SEQUENCE: 44
ctttgtatcg ataccatggt tatagaaggt gaaggaatat tag        43

<210> SEQ ID NO 45
<211> LENGTH: 37
<212> TYPE: DNA
<213> ORGANISM: Artificial Sequence
<220> FEATURE:
<223> OTHER INFORMATION: Description of Artificial Sequence: PRIMER

<400> SEQUENCE: 45
cacccagggc ccaaagactc cagttgaccc aaatccc              37

<210> SEQ ID NO 46
<211> LENGTH: 42
<212> TYPE: DNA
<213> ORGANISM: Artificial Sequence
<220> FEATURE:
<223> OTHER INFORMATION: Description of Artificial Sequence: PRIMER

<400> SEQUENCE: 46
gggtcaatcg atacaatgtc ttcatgggtg gacagaattg aa         42

<210> SEQ ID NO 47
<211> LENGTH: 38
<212> TYPE: DNA
<213> ORGANISM: Artificial Sequence
<220> FEATURE:
<223> OTHER INFORMATION: Description of Artificial Sequence: PRIMER

<400> SEQUENCE: 47
caatctgggc ccctcatcac cttcaggaag agtgcagg             38

<210> SEQ ID NO 48
<211> LENGTH: 32
<212> TYPE: DNA
<213> ORGANISM: Artificial Sequence
<220> FEATURE:
<223> OTHER INFORMATION: Description of Artificial Sequence: PRIMER

<400> SEQUENCE: 48
tgtagagcat ggtatcttga agcattagga aa                   32

<210> SEQ ID NO 49
<211> LENGTH: 35
<212> TYPE: DNA
<213> ORGANISM: Artificial Sequence
<220> FEATURE:
<223> OTHER INFORMATION: Description of Artificial Sequence: PRIMER

<400> SEQUENCE: 49
gttcctctct ttccgcctcc tactccaatc atatt                35

<210> SEQ ID NO 50
<211> LENGTH: 113
<212> TYPE: DNA
<213> ORGANISM: Artificial Sequence
<220> FEATURE:
<223> OTHER INFORMATION: Description of Artificial Sequence:Multiple
      Cloning Sites -continued

```
<400> SEQUENCE: 50
gcggccgcaa gatatcgccc taggtaagat ctcgatcgat ttggtaccaa tcgcgacctt        60
aattaacagc tagcggattt aaatcagggc ccgggatact agtgagcggc cgc             113

<210> SEQ ID NO 51
<211> LENGTH: 108
<212> TYPE: DNA
<213> ORGANISM: Artificial Sequence
<220> FEATURE:
<223> OTHER INFORMATION: Description of Artificial Sequence:Multiple
      Cloning Sites

<400> SEQUENCE: 51
gcggccgcaa gatatcgccc taggtaagat ctcgatcgat ttggtaccaa tcgcgacctt        60
aattaacagc tagcggattt aaatcagggc ccactagtga gcggccgc                  108

<210> SEQ ID NO 52
<211> LENGTH: 42
<212> TYPE: DNA
<213> ORGANISM: Artificial Sequence
<220> FEATURE:
<223> OTHER INFORMATION: Description of Artificial Sequence:Epitope Tag
      and Stop Codon

<400> SEQUENCE: 52
atgcagtacc cctacgacgt ccccgactac gccatgcatt ga                         42
```

DNA VACCINE AGAINST FELINE IMMUNODEFICIENCY VIRUS

This application claims the benefit of U.S. Provisional Application Serial No. 60/138,999, filed Jun. 14, 1999.

1. FIELD OF THE INVENTION

The present invention is in the field of animal health, and is directed to vaccine compositions and diagnostics for disease. More particularly, the present invention relates to polynucleotide molecules that can be used as vaccine components against feline immunodeficiency virus.

2. BACKGROUND OF THE INVENTION

Feline immunodeficiency virus (FIV) infection in cats results in a disease syndrome similar to that caused in humans by human immunodeficiency virus-1 (HIV-1) infection. After infection of cats by FIV, disease progression begins with a transient acute phase illness (8 to 10 weeks), followed by a prolonged asymptomatic phase varying from weeks to years, and a terminal symptomatic phase (Ishida and Tomoda, 1990, Jpn. J. Vet Sci. 52:645–648; English et al., 1994, J. Infect. Dis. 170: 543–552). Similar to HIV-1 disease progression (Graziosi et al., 1993, Proc. Natl. Acad. Sci. 90:6405–6409; Baumberger et al., 1993, AIDS 7:S59–S64; Wei et al., 1995, Nature 373:117–122), FIV RNA load in plasma has been demonstrated to correlate with disease stage, and can predict disease progression in accelerated FIV infection (Diehl et al., 1995, J. Virol. 69:2328–2332; Diehl et al., 1996, J. Virol. 70:2503–2507).

Based on the genetic diversity of the ENV protein of FIV, especially the V3 region, five FIV subtypes have been proposed: subtypes A and B, mainly in North America, Europe and Japan; subtype C in British Columbia and Taiwan; subtype D in Japan; and subtype E in Argentina (Sodora et al., 1994, J. Virol. 68:2230–2238; Kakinuma et al., 1995, J. Virol. 69:3639–3646; and Pecoraro et al., 1996, J. Gen. Virol. 77:2031–2035).

Similar to other lentiviruses, such as HIV-1, the FIV genome contains three large open reading frames, i.e., GAG (group antigens), ENV (envelope), and POL (polymerase), and three small open reading frames encoding regulatory (i.e., non-structural) proteins, i.e., Rev (regulator of expression of virion protein), Vif (virion infectivity factor) and ORF2 (open reading frame 2). The provirus contains two long terminal repeats (LTR), one at each end of the genome (Talbott et al., 1989, Proc. Natl. Acad. Sci. USA 86:5743–5747; Olmsted et al., 1989, Proc. Natl. Acad. Sci. USA 86:8088–8092). GAG is a precursor polyprotein that is processed into three mature virion structural proteins, i.e., the matrix (MA), capsid (CA) and nucleocapsid (NC) proteins. ENV is a precursor protein that is processed into two envelope structural proteins, i.e., the surface (SU) and transmembrane (TM) proteins. POL encodes four enzymatic (i.e., non-structural) proteins, i.e., protease (PR), reverse transcriptase (RT), deoxyuridine triphosphatase (DU) and integrase (IN).

The mechanism by which protective immunity against FIV infection can be achieved remains poorly understood. It has been reported by some groups that virus neutralizing (VN) antibodies appear to play a major role in the observed protection (Yamamoto et al., 1991, AIDS Res. Hum. Retrovir. 7:911–922; Hosie et al., 1995, J. Virol. 69:1253–1255). Consistent with those observations was the finding that cats who passively received antibodies from vaccinated or infected cats were protected from homologous challenge (Hohdatsu et al., 1993, J. Virol. 67:2344–2348; Pu et al., 1995, AIDS 9:235–242).

By contrast, convincing data also indicates that the levels of antibodies, or even VN antibodies, do not correlate with protection. It has been reported that cats were protected against homologous challenge in the absence of detectable VN antibodies (Verschoor et al., 1995, Vet. Immunol. Immunopathol. 46:139–149; Matteucci et al., 1996, J. Virol. 70:617–622). In addition, other vaccinated cats failed to be protected in the presence of significant VN antibodies (Huisman et al., 1998, Vaccine 16:181–187; Flynn et al., 1997 J. Virol. 71:7586–7592; Tijhaar et al., 1997, Vaccine 15:587–596; Osterhaus et al., 1996, AIDS Res. Hum. Retrovir. 12:437–441; Verschoor et al., 1996, Vaccine 14:285–289; Rigby et al., 1996, Vaccine 14:1095–1102; Lutz et al., 1995, Vet. Immunol. Immunopathol. 46:103–113; Flynn et al., 1995, Immunol. 85:171–175; Gonin et al., 1995, Vet. Microbiol. 45:393–401). This discrepancy appears to result, at least partially, from the different cell systems and virus isolates used in the VN assays. It has recently become evident that fresh isolates of FIV obtained from naturally infected cats are much less sensitive to VN antibodies than laboratory viruses adapted to growth in tissue culture (Baldinotti et al., 1994, J. Virol. 68: 4572–4579). It has also been found that the same antibodies which neutralized FIV infection in Crandell Feline Kidney (CRFK) cells failed to neutralize FIV infection in primary feline thymocytes (Huisman et al., 1998, above). These data indicate that the VN antibodies detected in vitro may not play any role in protective immunity in vivo.

In a few limited reports, cell-mediated immunity was investigated following vaccination. In one report, it was found that cellular immunity, especially ENV-specific CTL responses, played a major role in protecting cats vaccinated with whole inactivated virus (Flynn et al., 1996, J. Immunol. 157:3658–3665; Flynn et al., 1995, AIDS Res. Hum. Retrovir. 11:1107–1113). It was also reported that long-term protection was more closely correlated with the induction of ENV-specific cytotoxic T-cell activity (Hosie and Flynn, 1996, J. Virol. 70:7561–7568).

It appears that both humoral and cellular immunity are involved in achieving protective immunity in the acute phase after challenge, but for long-term protection, cell-mediated immunity appears to be more important. However, the question still remains which viral protein(s) or subunit(s) or combinations are capable of inducing protective immune responses. In one report, although both cell-mediated and humoral immune responses were induced in cats vaccinated with a multi-epitopic peptide within the ENV protein, vaccination did not confer protection against homologous challenge (Flynn et al., 1997, above).

As in HIV-1, an observation that complicates the development of an effective FIV vaccine is the enhancement of infection that has been observed in cats immunized with certain vaccines. Such enhancement of infection has been observed in a number of FIV vaccine trials in which either recombinant subunit vaccines, synthetic vaccines, whole inactivated virus vaccines or fixed, infected cell vaccines were used to vaccinate cats (Osterhaus et al., 1996, above; Siebelink et al., 1995, J. Virol. 69:3704–3711; Lombardi et al., 1994, J. Virol. 68:8374–8379; Hosie et al., 1992, Vet. Immunol. Immunopathol. 35:191–197; Huisman et al., 1998, above). For example, in an ENV subunit vaccine trial, enhancement of infection occurred despite anti-ENV and VN antibody production, and this enhancement could be transferred to naive cats via plasma pools from the vaccinated animals, indicating that the enhancement was probably mediated by specific antibodies (Siebelink et al., 1995, above).

It appears that antibodies against ENV tend to enhance infection more readily than antibodies against GAG protein. However, the mechanism by which antibodies enhance FIV infection remains poorly understood. In HIV-1, antibody-dependent enhancement requires that the target cells express either the immunoglobulin Fc receptor (FcR), or complement receptors (CRs). The enhancement is a biphasic response based on serum dilution; that is, at higher antibody concentrations, viral neutralization is observed, whereas enhancement is seen at lower antibody concentrations (Mascola et al., 1993, AIDS Res. Hum. Retrovir. 9:1175–1184). The enhanced infectivity may interfere with the induction of protective immunity in FIV, which may partially explain the reason why a large number of FIV vaccination experiments in which ENV protein or its subunits were used as vaccines were unsuccessful. Therefore, the rational development of vaccines against lentiviruses, including FIV and HIV-1, requires the careful assessment and selection of vaccine immunogens.

Since the discovery of FIV, many attempts have been made to develop a safe and effective FIV vaccine. Three different groups have attempted to vaccinate cats with fixed virus-infected cells; however, conflicting results were obtained from these vaccination trials. The first group found that all the cats vaccinated with fixed FIV-infected cells were protected from challenge with plasma obtained from cats infected with the homologous virus, despite the fact that no VN antibodies were detected after vaccination (Matteucci et al., 1996, above). The protection conferred by this vaccine, however, was relatively short-lived and difficult to boost (Matteucci et al., 1997, J. Virol. 71:8368–8376). Similar results were reported by the second group describing protection against homologous, but not heterologous, FIV challenge up to 12 weeks post-challenge (Bishop et al., 1996, Vaccine 14:1243–1250). However, when cats were monitored up to week 50 post-challenge, a loss of protection against the homologous virus was observed. Also, protection could not be correlated with the levels of antibody to p24 capsid protein or VN titers. In contrast to these findings, the third group reported no protection when ten cats were vaccinated with a fixed FIV-infected cell vaccine. Eight of the cats became viraemic 5 weeks post-challenge, although significant VN antibodies were detected at the time of challenge (Verschoor et al., 1995, above).

Another type of conventional FIV vaccine that has been tested is whole, inactivated virus. The first successful whole-inactivated FIV vaccine was reported by Yamamoto's group, which observed greater than 90% protection against homologous challenge (Yamamoto et al., 1991, AIDS Res. Hum. Retrovir. 7:911–922), and slight protection against heterologous challenge (Yamamoto et al., 1993, J. Virol. 67:601–605). Both humoral and cellular immunity against FIV were induced and high levels of anti-ENV, anti-core, and VN antibodies were observed in the vaccinated cats. Recent studies have indicated that both virus-specific humoral immunity, especially VN antibodies, and cellular immunity, especially the ENV-specific CTL responses, play a role in the protection induced in cats vaccinated with whole, inactivated virus (Hosie and Flynn, 1996, above; Flynn et al., 1996, above; Hosie et al., 1995, above; Elyar et al., 1997, Vaccine 15:1437–1444). However, in contrast to the studies described above, vaccination of cats with whole, inactivated FIV incorporated into immune stimulating complexes (ISCOMS) failed to protect against homologous challenge (Hosie et al., 1992, above).

Another approach for FIV vaccine development that has been extensively investigated recently is recombinant vaccines. A number of FIV subunit vaccines have been tested, including those containing recombinant core protein, synthetic V3, or multi-epitopic peptides, glycosylated or unglycosylated recombinant ENV protein, and various vector-based systems (Elyar et al., 1997, above). Unfortunately, although significant levels of antibodies were generally induced by such vaccinations, all attempts failed to protect vaccinated cats against homologous challenge (Huisman et al., 1998, above; Flynn et al., 1997, above; Tijhaar et al., 1997, above; Osterhaus et al., 1996, above; Verschoor et al., 1996, above; Rigby et al., 1996, above; Lutz et al., 1995, above; Flynn et al., 1995, Immunol. 85:171–175; Gonin et al., 1995, above).

Recently, a DNA vaccine was tested for FIV. Cats vaccinated with plasmid DNA carrying FIV structural genes, including ENV and p10 gene (i.e., the NC protein of FIV), exhibited strong humoral immune responses. However, none of the vaccinated cats were protected from homologous challenge (Cuisinier et al., 1997, Vaccine 15: 1085–1094).

In addition, WO 98/03660 describes various formulae for feline polynucleotide vaccines including against FIV, but only mentions the use of ENV polyprotein and GAG/PRO polyprotein genes, and does not describe the use of other FIV genes, or substituent genes from the particular polyprotein genes, nor does it provide any data showing efficacy of any particular FIV vaccine.

3. SUMMARY OF THE INVENTION

The present invention provides a vaccine composition against feline immunodeficiency virus (FIV), comprising an immunologically effective amount of a polynucleotide molecule comprising a nucleotide sequence selected from a portion of the genome of an FIV strain, or a nucleotide sequence which is a degenerate variant thereof; and a veterinarily acceptable carrier. The FIV strain can be any strain of FIV, but is preferably strain FIV-141 having a genomic RNA sequence corresponding to the DNA sequence shown in SEQ ID NO:1 from nt 1 to nt 9464.

In a preferred embodiment, the polynucleotide molecule of the vaccine composition comprises a nucleotide sequence encoding one or more of a structural or non-structural protein from an FIV strain, or a combination thereof. The structural protein is selected from the group consisting of a GAG protein and an ENV protein. The non-structural protein is selected from the group consisting of a POL protein and a regulatory protein. The GAG protein is selected from the group consisting of the GAG polyprotein and its substituent proteins, i.e., MA, CA and NC. The ENV protein is selected from the group consisting of the ENV polyprotein and its substituent proteins, i.e., SU and TM. The POL protein is selected from the group consisting of the POL polyprotein and its substituent proteins, i.e., PR, RT, DU and IN. The regulatory protein is selected from the group consisting of Rev, Vif and ORF2.

The polynucleotide molecule of the vaccine composition may alternatively or additionally comprise a nucleotide sequence consisting of a substantial portion of any of the aforementioned nucleotide sequences. In a preferred embodiment, the substantial portion of the nucleotide sequence encodes an epitope of an FIV protein.

In a preferred embodiment, the vaccine composition of the present invention comprises a polynucleotide molecule comprising a nucleotide sequence encoding an FIV protein selected from the group consisting of GAG, MA, CA, NC, ENV, SU, TM, DU and PR.

In a more preferred embodiment, the vaccine composition of the present invention is a combination vaccine, which comprises one or more polynucleotide molecules having nucleotide sequences encoding a combination of FIV proteins. In a preferred embodiment, the one or more polynucleotide molecules of the vaccine composition comprise nucleotide sequences encoding at least two different FIV proteins selected from FIV structural and FIV non-structural proteins, provided that when the one or more polynucleotide molecules encode the ENV and NC proteins from FIV, they also encode at least one, preferably at least two, and most preferably at least three other FIV structural or non-structural proteins.

In a further preferred embodiment, the one or more polynucleotide molecules of the vaccine composition comprise nucleotide sequences encoding at least two different GAG proteins from FIV.

In a further preferred embodiment, the one or more polynucleotide molecules of the vaccine composition comprise nucleotide sequences encoding at least one FIV structural protein and at least one FIV non-structural protein.

In a further preferred embodiment, the one or more polynucleotide molecules of the vaccine composition comprise nucleotide sequences encoding at least three different FIV proteins selected from among the FIV structural and FIV non-structural proteins, i.e., the proteins can be either all structural proteins or all non-structural proteins, or a combination of structural and non-structural proteins. In a further preferred embodiment, the one or more polynucleotide molecules of the vaccine composition comprise nucleotide sequences encoding at least four different FIV proteins selected from among the FIV structural and FIV non-structural proteins. In a further preferred embodiment, the one or more polynucleotide molecules of the vaccine composition comprise nucleotide sequences encoding at least five different FIV proteins selected from among the FIV structural and FIV non-structural proteins. In a further preferred embodiment, the one or more polynucleotide molecules of the vaccine composition comprise nucleotide sequences encoding at least six different FIV proteins selected from among the FIV structural and FIV non-structural proteins. In a further preferred embodiment, the one or more polynucleotide molecules of the vaccine composition comprise nucleotide sequences encoding at least seven different FIV proteins selected from among the FIV structural and FIV non-structural proteins.

In a further preferred embodiment, the one or more polynucleotide molecules of the vaccine composition comprise a nucleotide sequence encoding at least one FIV structural protein and a nucleotide sequence encoding at least one FIV regulatory protein. In a further preferred embodiment, the one or more polynucleotide molecules of the vaccine composition comprise a nucleotide sequence encoding at least one FIV POL protein and a nucleotide sequence encoding at least one FIV regulatory gene. In a further preferred embodiment, the one or more polynucleotide molecules of the vaccine composition comprise a nucleotide sequence encoding at least one FIV structural protein, a nucleotide sequence encoding at least one FIV POL protein, and a nucleotide sequence encoding at least one FIV regulatory protein.

In a further preferred embodiment, when the one or more polynucleotide molecules of the vaccine composition comprise nucleotide sequences encoding a GAG protein, PR protein or ENV protein from FIV, or a combination thereof, one or more nucleotide sequences encoding at least one, more preferably at least two, and most preferably at least three other FIV proteins are present.

In a particularly preferred embodiment, the vaccine composition of the present invention comprises one or more polynucleotide molecules comprising nucleotide sequences encoding a combination of FIV proteins, which combination is selected from the group consisting of GAG/MA/CA/NC; GAG/ENV; GAG/MA/CA/NC/ENV/SU/TM; MA/CA/NC; GAG/MA/NC/DU/PR; and MA/CA/NC/SU/TM. When the vaccine composition of the present invention is a combination vaccine, the nucleotide sequences encoding the various FIV proteins or polypeptides can be on the same polynucleotide molecule, on different polynucleotide molecules, or a combination thereof.

The polynucleotide molecule of the vaccine composition can either be a DNA or RNA molecule, although DNA is preferred. The polynucleotide molecule of the vaccine composition is preferably administered as part of an expression vector construct, such as a plasmid or a viral vector.

The present invention further provides a method of preparing a vaccine composition against FIV, comprising combining an immunologically effective amount of any one or more of the aforementioned polynucleotide molecules, or any one or more expression vectors comprising such polynucleotide molecules, with a veterinarily acceptable carrier in a form suitable for administration to cats. In a non-limiting embodiment, a veterinarily acceptable carrier is selected from standard aqueous or partially aqueous solutions, such as sterile saline or PBS, or cationic lipid preparations, or gold microparticles onto which the one or more polynucleotide molecules or expression vectors of the vaccine composition can be coated and administered to an animal for vaccine delivery. The vaccine composition can further comprise a supplemental component such as, e.g., an immunomodulatory agent, which can be an adjuvant, or a cytokine, or a polynucleotide molecule having a nucleotide sequence encoding a cytokine; or an agent which facilitates cellular uptake by the vaccinated animal of the polynucleotide molecule or expression vector; or a combination thereof.

The present invention further provides a method of vaccinating a cat against FIV, comprising administering to the cat a vaccine composition of the present invention. In a preferred though non-limiting embodiment, the vaccine composition of the present invention is administered to a cat either by intramuscular or intradermal injection, or orally, intranasally, or by use of a gene gun.

The present invention further provides a kit for vaccinating a cat against FIV, comprising a first container comprising an immunologically effective amount of any one or more of the aforementioned polynucleotide molecules or expression vectors of the present invention. In a non-limiting embodiment, the one or more polynucleotide molecule or expression vectors are stored in the first container in lyophilized form. The kit may optionally further comprise a second container comprising a sterile diluent useful to dilute or rehydrate the polynucleotide molecules or expression vectors in the first container for administration to a cat.

The present invention further provides an isolated antibody that binds specifically to an FIV protein, which antibody is produced in a mammal in response to administration of a polynucleotide molecule having a nucleotide sequence encoding the FIV protein or an epitope thereof, such as, e.g., a polynucleotide molecule or expression vector as present in the vaccine composition of the present invention.

The present invention further provides a vaccine composition against FIV, comprising an immunologically effective amount of a GAG protein, POL protein, ENV protein, regulatory protein, or a combination thereof, from an FIV strain. The FIV strain can be any strain of FIV, but is preferably strain FIV-141. The GAG protein is preferably selected from the group consisting of the GAG polyprotein and its substituent proteins, i.e., MA, CA and NC. The POL protein is preferably selected from the group consisting of the POL polyprotein and its substituent proteins, i.e., PR, RT, DU and IN. The ENV protein is preferably selected from the group consisting of the ENV polyprotein and its substituent proteins, i.e., SU and TM. The regulatory protein is selected from the group consisting of Rev, Vif and ORF2.

In a more preferred embodiment, the vaccine composition of the present invention comprises a combination of FIV proteins. In a preferred embodiment, the proteins of the vaccine composition comprise at least two different FIV proteins selected from among the FIV structural and FIV non-structural proteins. In a further preferred embodiment, the proteins of the vaccine composition comprise at least two different GAG proteins from FIV. In a further preferred embodiment, the proteins of the vaccine composition comprise at least one FIV structural protein and at least one FIV non-structural protein. In a further preferred embodiment, the proteins of the vaccine composition comprise at least three different FIV proteins selected from among the FIV structural and FIV non-structural proteins. In a further preferred embodiment, the proteins of the vaccine composition comprise at least four different FIV proteins selected from among the FIV structural and FIV non-structural proteins. In a further preferred embodiment, the proteins of the vaccine composition comprise at least five different FIV proteins selected from among the FIV structural and FIV non-structural proteins. In a further preferred embodiment, the proteins of the vaccine composition comprise at least six different FIV proteins selected from among the FIV structural and FIV non-structural proteins. In a further preferred embodiment, the proteins of the vaccine composition comprise at least seven different FIV proteins selected from among the FIV structural and FIV non-structural proteins.

In a particularly preferred embodiment, the combination of FIV proteins is selected from the group consisting of GAG/MA/CA/NC; GAG/ENV; GAG/MA/CA/NC/ENV/SU/TM; MA/CA/NC; GAG/MA/NC/DU/PR; and MA/CA/NC/SU/TM.

Alternatively or additionally, the vaccine composition may comprise one or more polypeptides, one or more of which is a substantial portion of an FIV protein. In a preferred embodiment, the substantial portion of the FIV protein comprises an epitope of an FIV protein.

The vaccine composition of the present invention may alternatively comprise an immunologically effective amount of any one or more of the aforementioned polynucleotide molecules or expression vectors in combination with any one or more of the aforementioned proteins or polypeptides.

The present invention further provides a method of preparing a vaccine composition against FIV, comprising combining an immunologically effective amount of any one or more of the aforementioned proteins or polypeptides with a veterinarily acceptable carrier in a form suitable for administration to cats. The vaccine composition can further comprise a supplemental component such as, e.g., an immunomodulatory agent, which can be an adjuvant, or a cytokine, or a polynucleotide molecule having a nucleotide sequence encoding a cytokine, or a combination thereof.

The present invention further provides a method of vaccinating a cat against FIV, comprising administering to the cat a vaccine composition comprising an immunologically effective amount of any one or more of the aforementioned proteins or polypeptides.

The present invention further comprises oligonucleotide molecules that can be used as primers to specifically amplify particular FIV genes or other FIV-related polynucleotide molecules, and as diagnostic probes to detect the present of an FIV-related polynucleotide molecule in a fluid or tissue sample collected from an animal infected with FIV. In a preferred embodiment, such oligonucleotide molecules comprise nucleotide sequences selected from the group consisting of SEQ ID NOS: 2 to 47, or the complements of said sequences.

4. BRIEF DESCRIPTION OF THE DRAWINGS

FIG. 1. Genomic organization of the feline immunodeficiency virus.

Figure 2:
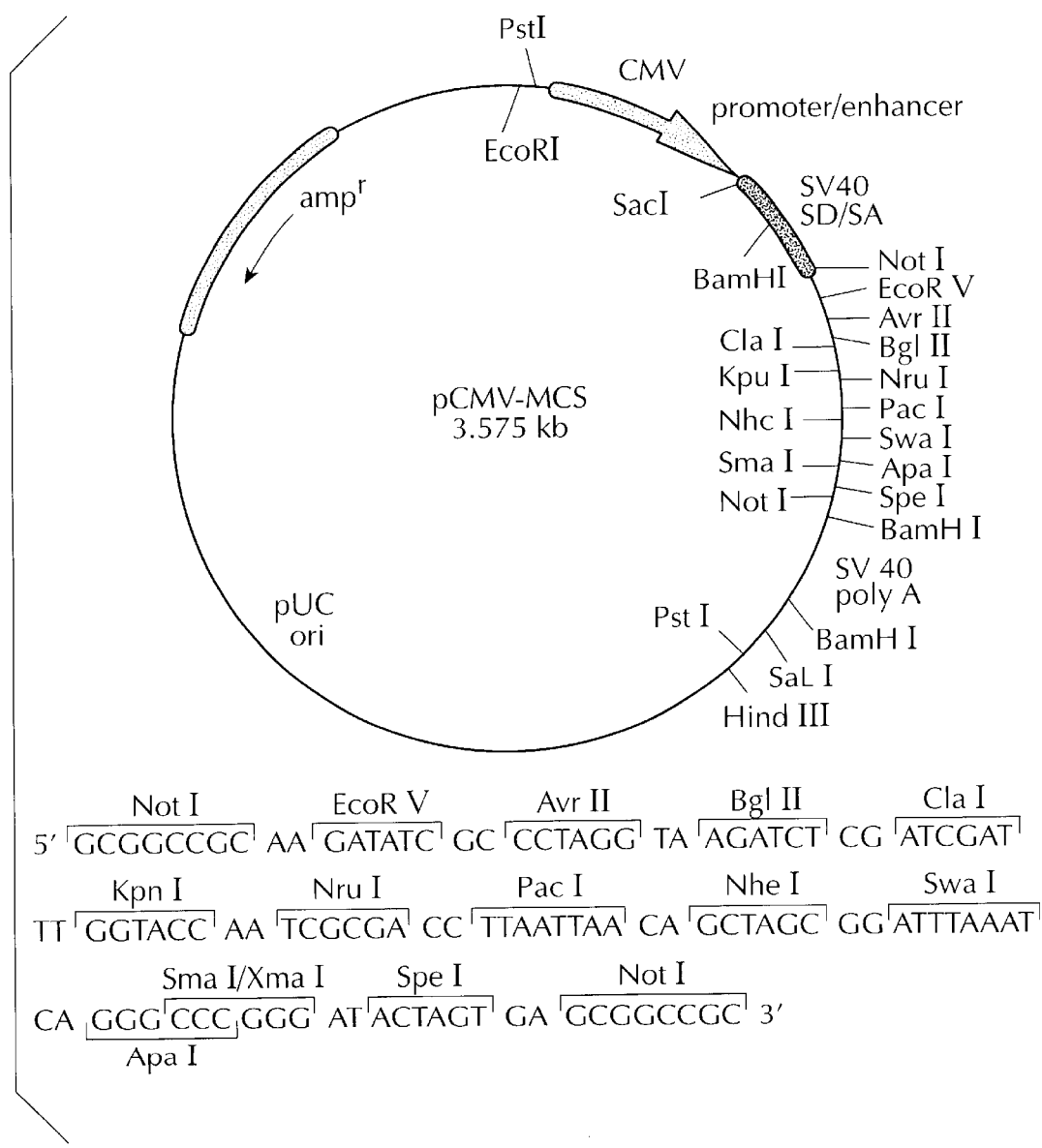

FIG. 2. Expression vector pCMV-MCS, generated from a synthetic DNA fragment containing multiple cloning sites (MCS) referred to herein as SEQ ID NO:50.

Figure 3:
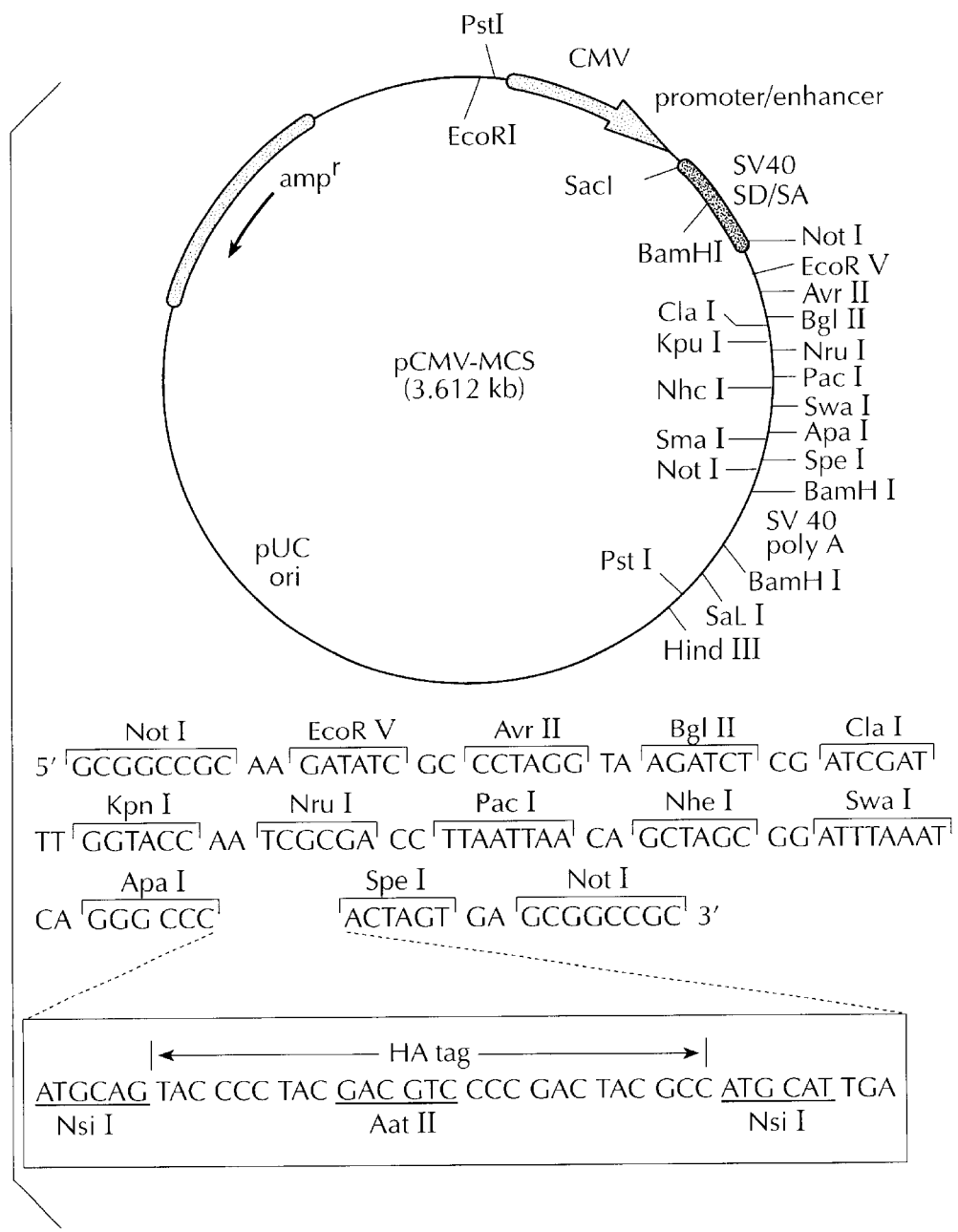

FIG. 3. Expression vector pCMV-HA, generated from a synthetic DNA fragment containing multiple cloning sites (MCS) referred to herein as SEQ ID NO:51 and a DNA fragment referred to herein as SEQ ID NO:52, containing an epitope tag from human influenza hemaglutinin and a translation stop codon.

Figure 4:
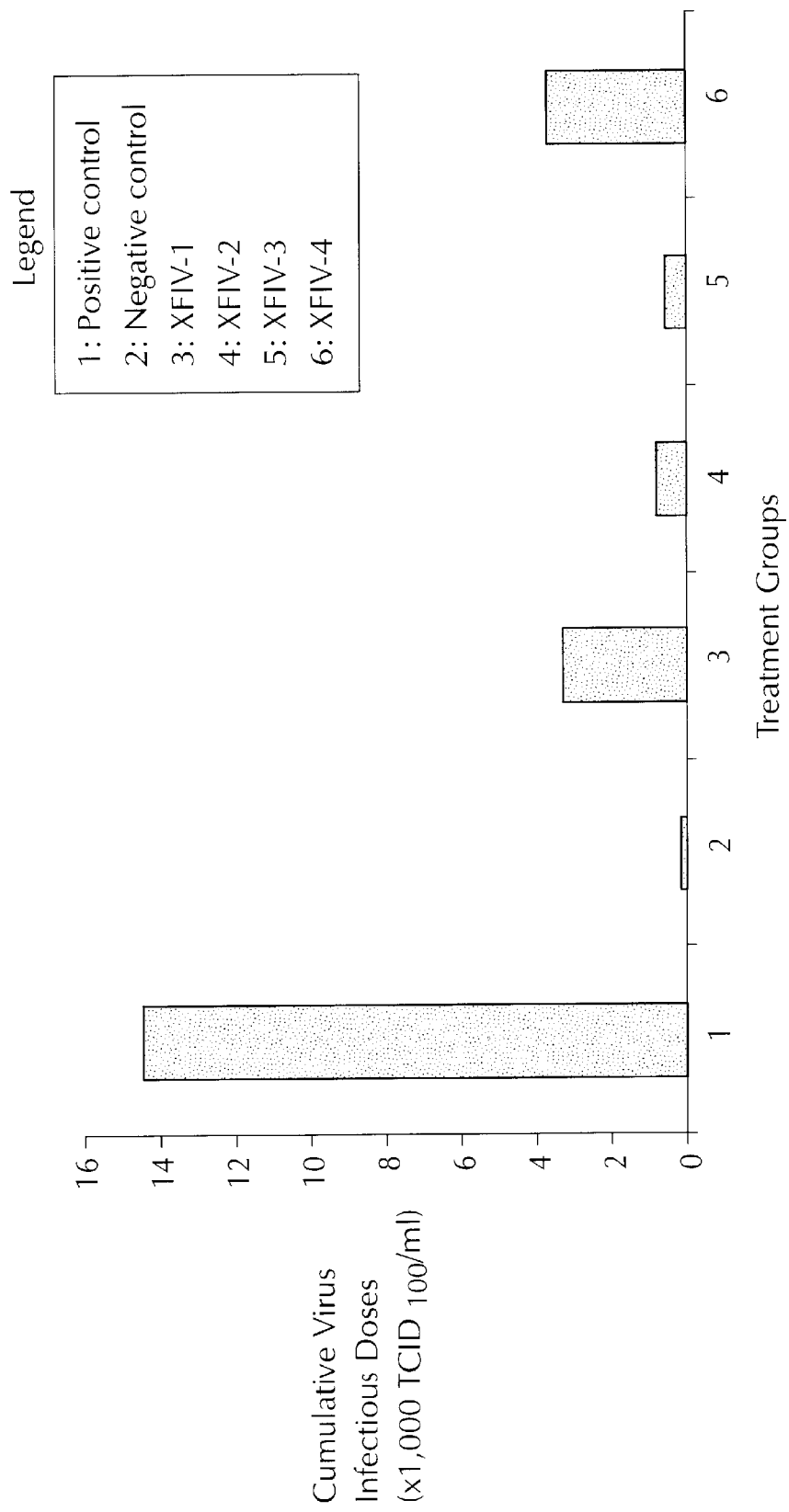

FIG. 4. Plasma viral load detected by virus isolation in the various vaccine treatment groups.

Figure 5:
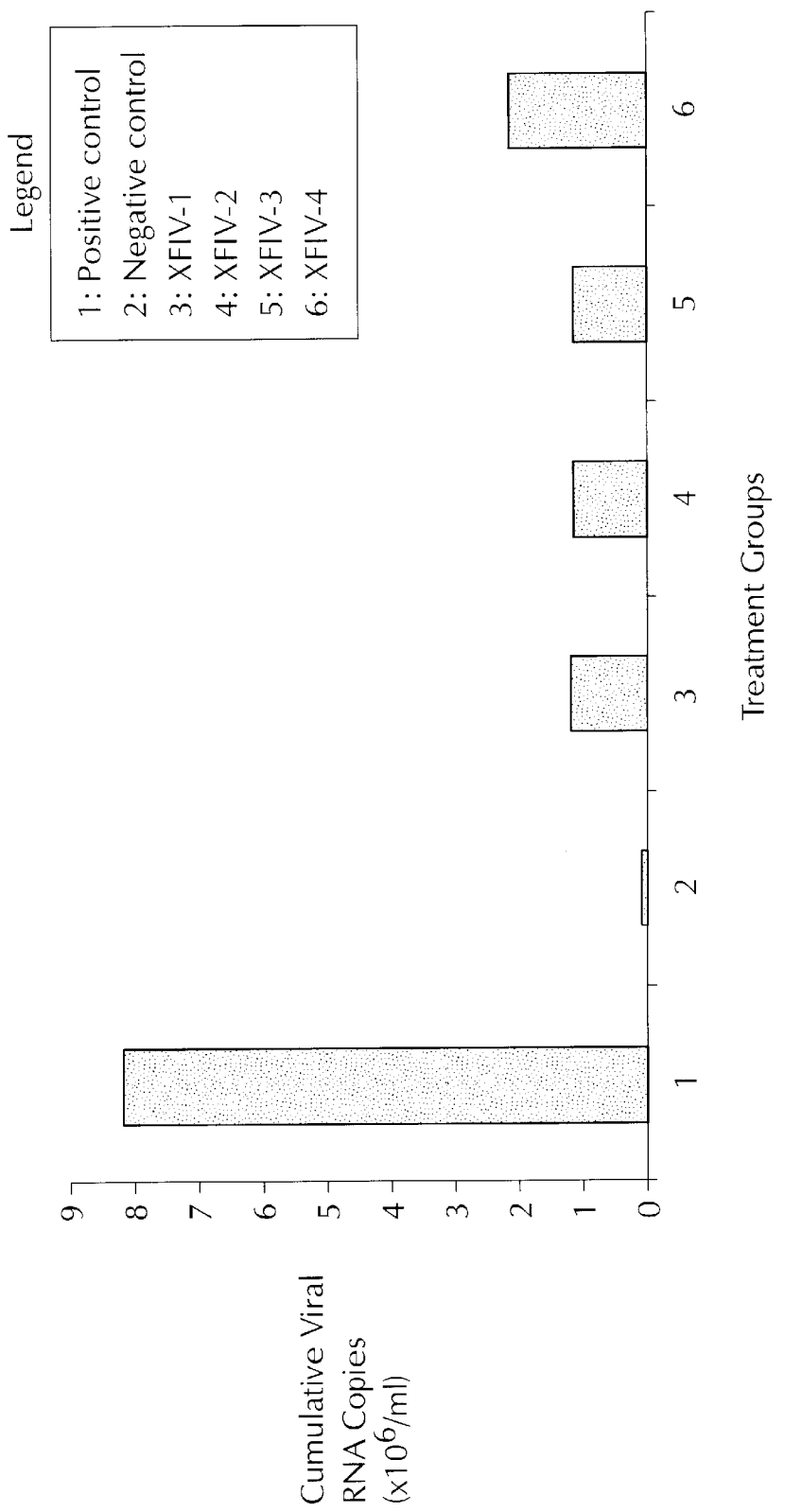

FIG. 5. Plasma viral load detected by QcRT-PCR in the various vaccine treatment groups.

Figure 6:
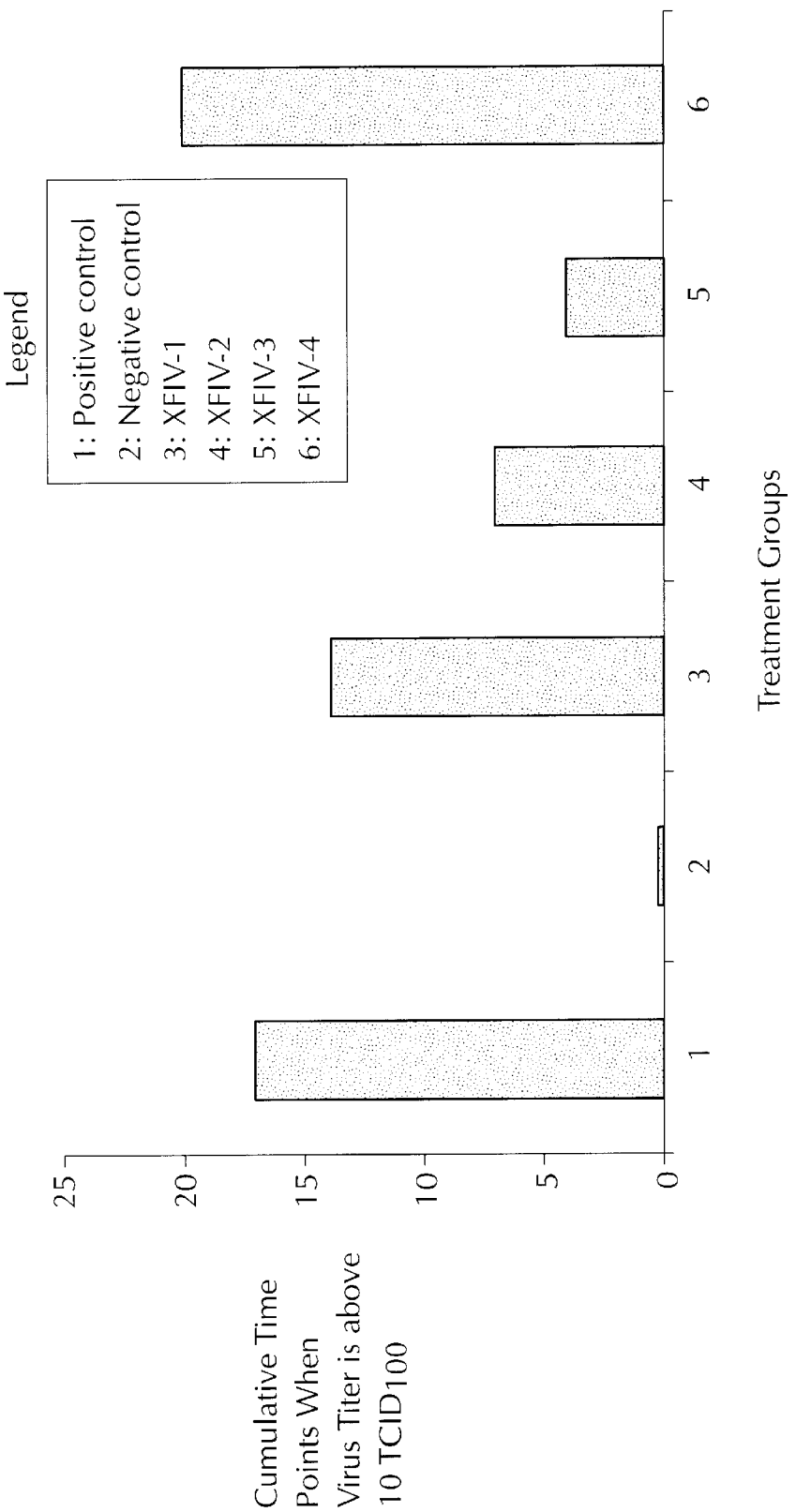

FIG. 6. Number of time points at which virus titer was above 10 $TCID_{100}$ in the various vaccine treatment groups, as detected by virus isolation.

Figure 7:
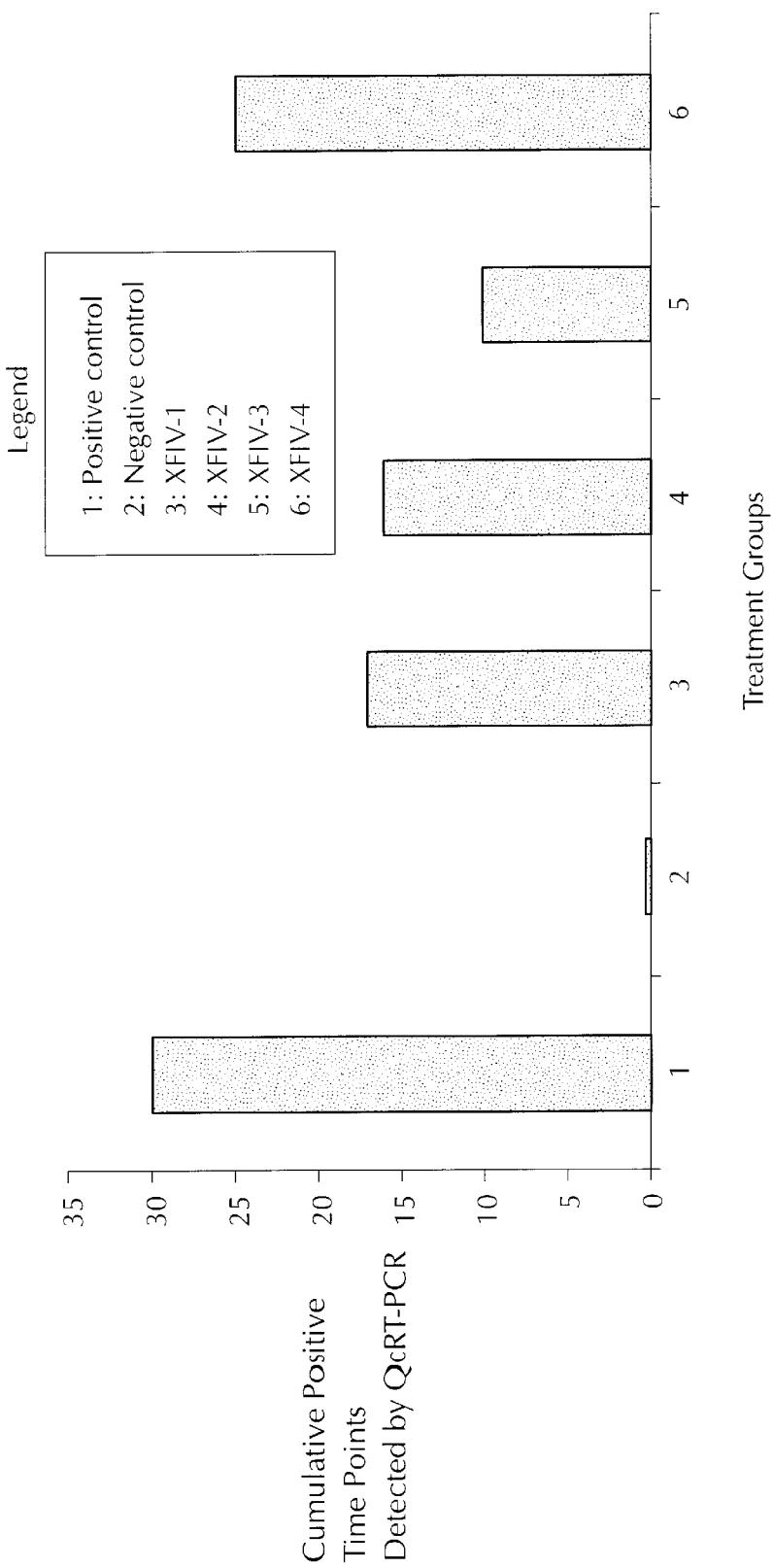

FIG. 7. Number of time points at which virus titer was above 10 $TCID_{100}$ in the various vaccine treatment groups, as detected by QcRT-PCR.

5. DETAILED DESCRIPTION OF THE INVENTION

5.1. DNA Vaccine 5.1.1. Polynucleotide Molecules

As used herein, the terms "DNA", "RNA", "gene," "polynucleotide molecule," "nucleotide sequence," "coding sequence," and "coding region" are intended to include both DNA and RNA polynucleotide molecules, and to refer to both single-stranded and double-stranded polynucleotide molecules. Thus, the term "DNA vaccine", as used herein, encompasses vaccines comprising either DNA or RNA, or both. Also, as used herein, the terms "gene," "coding sequence," and "coding region" are intended to refer to polynucleotide molecules that can be transcribed and translated (DNA), or translated (RNA), into an FIV structural or non-structural protein in a cat or in an appropriate in vitro host cell expression system when placed in operative association with appropriate regulatory elements. Polynucleotide molecules of the vaccine composition can include, but are not limited to, one or more prokaryotic sequences, eukaryotic sequences, cDNA sequences, genomic DNA sequences (exons and/or introns), and chemically synthesized DNA and RNA sequences, or any combination thereof.

The genome of FIV consists of RNA that is reverse transcribed into DNA and integrated into the genome of an infected feline host. Unless otherwise indicated, all references made herein to specific FIV genes and nucleotide sequences and, more generally, to polynucleotide molecules and nucleotide sequences, are intended to encompass both RNA sequences and DNA sequences that correspond thereto according to the complementary relationship between RNA and DNA sequences, as well as the complements of all such sequences.

Design, production and manipulation of the polynucleotide molecules, oligonucleotide molecules and expression vectors disclosed herein are within the skill in the art and can be carried out according to known genetic techniques which are described, among other places, in Maniatis et al., 1989, *Molecular Cloning, A Laboratory Manual*, Cold Spring Harbor Laboratory Press, Cold Spring Harbor, N.Y.; Ausubel et al., 1989, above; Sambrook et al., 1989, *Molecular Cloning: A Laboratory Manual*, 2d ed., Cold Spring Harbor Laboratory Press, Cold Spring Harbor, N.Y.; Innis et al. (eds), 1995, *PCR Strategies*, Academic Press, Inc., San Diego; and Erlich (ed), 1992, *PCR Technology*, Oxford University Press, New York, which are incorporated herein by reference.

The present invention provides a vaccine composition against feline immunodeficiency virus (FIV), comprising an immunologically effective amount of a polynucleotide molecule comprising a nucleotide sequence selected from a portion of the genome of an FIV strain, or a nucleotide sequence which is a degenerate variant thereof; and a veterinarily acceptable carrier. The FIV strain can be any strain of FIV currently known, or any strain to be isolated and identified in the future, and is preferably a pathogenic strain, In a preferred embodiment, the FIV strain is FIV-141, which has a genomic RNA sequence corresponding to the DNA sequence shown in SEQ ID NO:1 (from nt 1 to nt 9464). An infectious FIV-141 molecular plasmid clone and the FIV-141 virus were deposited on Jul. 1, 1998 with the American Type Culture Collection, and were assigned ATCC Accession Nos. 203001 and VR-2619, respectively. Alternatively, strains of FIV can be isolated from organs, tissues or body fluids of infected cats and propagated in tissue culture using standard isolation and tissue culture techniques such as those described in the publications reviewed above, and any such strains can be used to isolate polynucleotide molecules necessary to practice the present invention.

Reference is made to FIG. 1, which presents the overall genomic organization of FIV, and to the genomic sequence of FIV-141 presented in SEQ ID NO:1. In SEQ ID NO:1, the 5' LTR is from nt 1 to nt 354; the GAG polyprotein gene is from nt 627 to nt 1976; the POL polyprotein gene is from nt 1880 to nt 5239; Vif is from nt 5232 to nt 5987; ORF2 is from nt 5988 to nt 6224; the ENV gene is from nt 6262 to nt 8826; Rev is from nt 6262 to nt 6505, and from nt 8947 to nt 9161; and the 3' LTR is from nt 9111 to nt 9464. Within the GAG polyprotein gene, MA is encoded from nt 627 to nt 1031; CA is encoded from nt 1032 to nt 1724; and NC is encoded from nt 1725 to nt 1976. Within the POL polyprotein gene, PR is encoded from nt 1979 to nt 2326; RT is encoded from nt 2327 to nt 3994; DU is encoded from nt 3995 to nt 4393; and IN is encoded from nt 4394 to nt 5239. Within the ENV polyprotein gene, SU is encoded from nt 6262 to nt 8088; and TM is encoded from nt 8089 to nt 8826. The nucleotide boundaries presented herein also serve as a guide for selecting corresponding genes and coding regions of other FIV strains.

For polynucleotide molecules encoding structural or non-structural FIV proteins, including, e.g., a GAG protein, POL protein, ENV protein, ORF2, Vif, or Rev, or substantial portions thereof, a nucleotide sequence useful in practicing the present invention can be any sequence which encodes the particular protein or polypeptide, ie., either the native nucleotide sequence found in the particular FIV genome or, alternatively, a degenerate variant, i.e., a nucleotide sequence that encodes the same protein or polypeptide, but which differs from the native sequence as based on the degeneracy of the genetic code. The present invention encompasses vaccine compositions and methods of using polynucleotide molecules having any of these nucleotide sequences.

In a preferred embodiment, the polynucleotide molecule of the vaccine composition comprises a nucleotide sequence encoding one or more of a structural or non-structural protein from an FIV strain, or a combination thereof. The structural protein is selected from the group consisting of a GAG protein and an ENV protein. The non-structural protein is selected from the group consisting of a POL protein and a regulatory protein. The GAG protein is selected from the group consisting of the GAG polyprotein and its substituent proteins, ire., MA, CA and NC. The ENV protein is selected from the group consisting of the ENV polyprotein and its substituent proteins, i.e., SU and TM. The POL protein is selected from the group consisting of the POL polyprotein and its substituent proteins, i.e., PR, RT, DU and IN. The regulatory protein is selected from the group consisting of Rev, Vif, ORF2 and LTR.

In a preferred embodiment, the vaccine composition of the present invention comprises a polynucleotide molecule comprising a nucleotide sequence encoding an FIV protein selected from the group consisting of GAG, MA, CA, NC, ENV, SU, TM, DU and PR.

In a more preferred embodiment, the vaccine composition of the present invention is a combination vaccine, which comprises one or more polynucleotide molecules having nucleotide sequences encoding a combination of FIV proteins. In a preferred embodiment, the one or more polynucleotide molecules of the vaccine composition comprise nucleotide sequences encoding at least two different FIV proteins selected from FIV structural and FIV non-structural proteins, provided that when the one or more polynucleotide molecules encode the ENV and NC proteins from FIV, they also encode at least one, more preferably at least two, and most preferably at least three other FIV structural or non-structural proteins.

In a further preferred embodiment, the one or more polynucleotide molecules of the vaccine composition comprise nucleotide sequences encoding at least two different GAG proteins from FIV.

In a further preferred embodiment, the one or more polynucleotide molecules of the vaccine composition comprise nucleotide sequences encoding at least one FIV structural protein and at least one FIV non-structural protein.

In a further preferred embodiment, the one or more polynucleotide molecules of the vaccine composition comprise nucleotide sequences encoding at least three different FIV proteins selected from among the FIV structural and FIV non-structural proteins, i.e., the proteins can be either all structural proteins or all non-structural proteins, or a combination of structural and non-structural proteins. In a further preferred embodiment, the one or more polynucleotide molecules of the vaccine composition comprise nucleotide sequences encoding at least four different FIV proteins selected from among the FIV structural and FIV non-structural proteins. In a further preferred embodiment, the one or more polynucleotide molecules of the vaccine composition comprise nucleotide sequences encoding at least five different FIV proteins selected from among the FIV structural and FIV non-structural proteins. In a further preferred embodiment, the one or more polynucleotide molecules of the vaccine composition comprise nucleotide sequences encoding at least six different FIV proteins selected from among the FIV structural and FIV non-structural proteins. In a further preferred embodiment, the one or more polynucleotide molecules of the vaccine composition comprise nucleotide sequences encoding at least seven different FIV proteins selected from among the FIV structural and FIV non-structural proteins.

In a further preferred embodiment, the one or more polynucleotide molecules of the vaccine composition comprise a nucleotide sequence encoding at least one FIV structural protein and a nucleotide sequence encoding at least one FIV regulatory protein. In a further preferred embodiment, the one or more polynucleotide molecules of the vaccine composition comprise a nucleotide sequence encoding at least one FIV POL protein and a nucleotide sequence encoding at least one FIV regulatory gene. In a further preferred embodiment, the one or more polynucleotide molecules of the vaccine composition comprise a nucleotide sequence encoding at least one FIV structural protein, a nucleotide sequence encoding at least one FIV POL protein, and a nucleotide sequence encoding at least one FIV regulatory protein.

In a further preferred embodiment, when the one or more polynucleotide molecules of the vaccine composition comprise nucleotide sequences encoding a GAG protein, PR protein or ENV protein from FIV, or a combination thereof, nucleotide sequences encoding at least one, preferably at least two, and most preferably at least three, other FIV proteins are present.

In a particularly preferred embodiment, the vaccine composition of the present invention comprises one or more polynucleotide molecules comprising nucleotide sequences encoding a combination of FIV proteins, which combination is selected from the group consisting of GAG/MA/CA/NC; GAG/ENV; GAG/MA/CA/NC/ENV/SU/TM; MA/CA/NC; GAG/MA/NC/DU/PR; and MA/CA/NC/SU/TM. When the vaccine composition of the present invention is a combination vaccine, the nucleotide sequences encoding the various FIV proteins or polypeptides can be on the same polynucleotide molecule, on different polynucleotide molecules, or a combination thereof.

The vaccine composition may alternatively or additionally comprise one or more polynucleotide molecules comprising a nucleotide sequence which is a substantial portion of any of the aforementioned nucleotide sequences. As used herein, a nucleotide sequence is a "substantial portion" of a nucleotide sequence encoding a GAG protein, POL protein , ENV protein or regulatory protein from an FIV strain, where the nucleotide sequence consists of less than the complete nucleotide sequence encoding the particular full length FIV protein, but is at least about 30%, more preferably at least about 50%, and most preferably at least about 70% of the complete nucleotide sequence encoding the particular full length FIV protein, or a degenerate variant thereof, and is useful in practicing the present invention. In a preferred embodiment, the "substantial portion" of the nucleotide sequence encodes at least one epitope of an FIV antigen.

As used herein, a polynucleotide molecule is "useful in practicing the present invention" where: (1) the polynucleotide molecule, upon administration to a cat, can detectably induce a protective immune response against FIV, or can detectably enhance the induction of a protective immune response against FIV when co-administered to a cat with one or more other FIV antigen-encoding polynucleotide molecules or FIV proteins or polypeptides; (2) the polynucleotide molecule can be utilized in a recombinant in vitro expression system to prepare a protein or polypeptide which, upon administration to a cat can detectably induce a protective immune response against FIV, or can detectably enhance the induction of a protective immune response against FIV when co-administered to a cat with one or more FIV antigen-encoding polynucleotide molecules or one or more other FIV proteins or polypeptides; (3) the polynucleotide molecule, or the protein or polypeptide which is encoded thereby, can be used to induce the production of anti-FIV antibodies in a mammal; or (4) the polynucleotide molecule or its complement can be used as a diagnostic reagent to detect the presence of an FIV-specific polynucleotide molecule in a fluid or tissue sample from an FIV-infected cat. Such polynucleotide molecules can be prepared and identified using standard techniques known in the art.

As used herein, a protein or polypeptide is "useful in practicing the present invention" where: (1) the protein or polypeptide, upon administration to a cat, can detectably induce a protective immune response against FIV, or can detectably enhance the induction of a protective immune response against FIV when co-administered to a cat with one or more FIV antigen-encoding polynucleotide molecules or one or more other FIV proteins or polypeptides; (2) the polypeptide can be used to induce the production of anti-FIV antibodies in a mammal; or (3) the polypeptide can be used as a diagnostic reagent to detect the presence of FIV-specific antibodies in a fluid or tissue sample from an FIV-infected cat. Such polypeptides can be prepared and identified using standard techniques known in the art.

The polynucleotide molecule of the vaccine composition may alternatively or additionally comprise a nucleotide sequence encoding a polypeptide otherwise having the amino acid sequence of one or more of a GAG protein, POL protein, ENV protein or regulatory protein from an FIV strain, but in which one or more amino acid residues present in the native FIV protein has been conservatively substituted with a different amino acid residue, where the polynucleotide molecule is useful in practicing the present invention, as usefulness is defined above. Conservative amino acid substitutions, the nucleotide sequences that encode them, and the methods to prepare them are well known in the art. For example, a polynucleotide molecule can be prepared which encodes the conservative substitution of one or more amino acid residues of an FIV-141 protein, where the resulting polynucleotide molecule or encoded polypeptide is useful in practicing the present invention. Rules for making such substitutions include those described by Dayhof, M. D., 1978, Nat. Biomed. Res. Found., Washington, D.C., Vol. 5, Sup. 3, among others. More specifically, conservative amino acid substitutions are those that generally take place within a family of amino acids that are related in their side chains. Genetically encoded amino acids are generally divided into four groups: (1) acidic=aspartate, glutamate; (2) basic= lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan and tyrosine are also jointly classified as aromatic amino acids. One or more replacements within any particular group, e.g., of a leucine by isoleucine or valine, or of an aspartate by glutamate, or of a threonine by serine, or of any other amino acid residue by a structurally related amino acid residue, will generally have an insignificant effect on the usefulness of the resulting polypeptide in practicing the present invention. In a preferred embodiment, such a polypeptide having one or more conservative amino acid substitutions, as encoded by the polynucleotide molecule of the present invention, has at least about 70%, more preferably at least about 80% and most preferably at least about 90% sequence identity to the corresponding native FIV protein or polypeptide, and is useful in practicing the present invention.

In an alternative embodiment, the one or more polynucleotide molecules of the vaccine composition comprise a combination of any of the aforementioned nucleotide sequences.

The vaccine composition of the present invention can comprise at least two different polynucleotide molecules, wherein the first polynucleotide molecule comprises a nucleotide sequence encoding one or more FIV proteins or polypeptides as described above; and the second polynucleotide molecule comprises a nucleotide sequence encoding one or more FIV proteins or polypeptides that are different from those encoded by the first polynucleotide molecule, or encoding a different antigen useful in detectably inducing a protective response in cats either against FIV or against a different feline pathogen such as, e.g., feline leukemia virus (FeLV), feline calicivirus, or feline herpes virus, as known in the art.

Any of the polynucleotide molecules of the present invention can further comprise a nucleotide sequence encoding an immunomodulatory molecule such as a cytokine or a carrier protein, or the nucleotide sequence encoding the immunomodulatory molecule can be present on a different polynucleotide molecule which can be co-administered with a polynucleotide molecule of the present invention.

The polynucleotide molecule of the vaccine composition can either be DNA or RNA, although DNA is preferred, and is preferably administered to a cat in an expression vector construct, such as a recombinant plasmid or viral vector, as known in the art. Examples of recombinant viral vectors include recombinant adenovirus vectors and recombinant retrovirus vectors. However, a preferred vaccine formulation comprises a non-viral DNA vector, most preferably a DNA plasmid-based vector. The polynucleotide molecule may be associated with lipids to form, e.g., DNA-lipid complexes, such as liposomes or cochleates. See, e.g., International Patent Publications WO 93/24640 and WO 98/58630, which are incorporated herein by reference.

An expression vector useful as a vaccinal agent in a DNA vaccine will preferably comprise any of the aforementioned polynucleotide molecules of the present invention having an FIV-related nucleotide sequence. In a preferred embodiment, the expression vector comprises at least a nucleotide sequence encoding one or more antigenic FIV proteins, or a substantial portion of such a nucleotide sequence, in operative association with one or more transcriptional regulatory elements required for expression of the FIV coding sequence in a eukaryotic cell, such as, e.g., a promoter sequence, as known in the art. In a preferred embodiment, the regulatory element is a strong viral promoter such as, e.g., a viral promoter from RSV, CMV, or SV40, or the LTR promoter from a retrovirus, as known in the art. Such an expression vector also preferably includes a bacterial origin of replication and a prokaryotic selectable marker gene for cloning purposes, and a polyadenylation sequence to ensure appropriate termination of the expressed mRNA. A signal sequence may also be included to direct cellular secretion of the expressed protein.

The requirements for expression vectors useful as vaccinal agents in DNA vaccines are further described, among other places, in U.S. Pat. No. 5,703,055, U.S. Pat. No. 5,580,859, U.S. Pat. No. 5,589,466, International Patent Publication WO 98/35562, and in various scientific publications, including Ramsay et al., 1997, Immunol. Cell Biol. 75:360–363; Davis, 1997, Cur. Opinion Biotech. 8:635–640; Manickan et al., 1997, Critical Rev. Immunol. 17:139–154; Robinson, 1997, Vaccine 15(8):785–787; Robinson et al., 1996, AIDS Res. Hum. Retr. 12(5):455–457; Lai and Bennett, 1998, Critical Rev. Immunol. 18:449–484; and Vogel and Sarver, 1995, Clin. Microbiol. Rev. 8(3):406–410, which are incorporated herein by reference.

5.1.2. DNA Vaccine Formulation and Use

The present invention further provides a method of preparing a vaccine composition against FIV, comprising combining an immunologically effective amount of any one or more of the aforementioned FIV-related polynucleotide molecules, or any one or more expression vectors comprising such polynucleotide molecules, with a veterinarily acceptable carrier in a form suitable for administration to a cat.

As used herein, the term "immunologically effective amount", as it relates to an FIV-related polynucleotide molecule, expression vector, protein or polypeptide, refers to that amount of polynucleotide molecule, expression vector, protein or polypeptide, respectively, capable of inducing, or enhancing the induction of, a protective response against FIV when administered to a cat.

As used herein, the phrase "capable of inducing a protective response against FIV", and the like, is used broadly to include the induction of any immune-based response in the cat in response to vaccination, including either an antibody or cell-mediated immune response, or both, that serves to protect the vaccinated animal against FIV.

As used herein, a polynucleotide molecule, expression vector, protein or polypeptide "can enhance the induction of a protective immune response against FIV" when its addition to an FIV vaccine composition comprising one or more other FIV antigen-encoding polynucleotide molecules, proteins or polypeptides serves to detectably increase the protective response against FIV that would otherwise be induced by a vaccine combination without such an addition.

The terms "protective response" and "protect" as used herein refer not only to the absolute prevention of any of the symptoms or conditions resulting from FIV infection in cats, but also to any detectable delay in the onset of any such symptoms or conditions, any detectable reduction in the degree or rate of infection by FIV, or any detectable reduction in the severity of the disease or any symptom or condition resulting from infection by FIV, including, e.g., any detectable reduction in viral load, CD4/CD8 T lymphocyte ratio, mortality, etc., as compared to an FIV-infected animal (i.e., a control). The immunologically effective amount of the one or more polynucleotide molecules, expression vectors, or FIV proteins or polypeptides, may be administered either in a single dose or in divided doses. For purposes of the present invention, a protective response is deemed to have been induced if it can be detected after administration of the single complete dose, or after administration to the animal of all of the divided doses. The present invention further encompasses the administration to a previously vaccinated cat of an additional "booster" dose to increase the protective response against FIV.

In a preferred embodiment, the vaccine composition of the present invention is capable of inducing a protective response in a cat against homologous challenge, i.e., a cat vaccinated with the vaccine composition exhibits a protective response against a strain of the same sub-type of FIV from which the antigenic components of the vaccine composition were prepared or derived.

In a more preferred embodiment, the vaccine composition of the present invention is capable of inducing a protective response in a cat against heterologous challenge, i.e., a cat vaccinated with the vaccine composition exhibits a protective response against a strain of a different sub-type of FIV from which the antigenic components of the vaccine composition were prepared or derived.

The vaccine composition of the present invention will typically be adapted for intradermal or intramuscular injection, although other routes (e.g., intravenous, intraperitoneal, intranasal, oral, intraocular, rectal, vaginal) can also be effective. Veterinarily acceptable carriers can be any carriers known in the art that are compatible with DNA vaccines, as described in the publications cited herein. The vaccine composition of the present invention can be formulated following accepted convention using standard buffers, carriers, stabilizers, diluents, preservatives and/or solubilizers, and can also be formulated to facilitate sustained release. For example, the polynucleotide molecule of the vaccine composition can be prepared in aqueous solution, such as in sterile saline or PBS solution, or incorporated into liposomes or cochleates for parenteral administration. See, e.g., International Patent Publication WO 93/24640 or U.S. Pat. No. 5,703,055. Suitable other vaccine vehicles and additives that are particularly useful in DNA vaccine formulations are known or will be apparent to those of skill in the art. Alternatively, the polynucleotide molecule of the vaccine composition can be coated onto metallic particles, such as gold particles, for administration to a cat using a "gene gun." See, e.g., Tang et al., 1992, Nature 356:152–154. Thus, for purposes of this invention, metallic particles, such as gold particles, onto which polynucleotide molecules or expression vectors of the present invention can be coated and administered to cats are also considered to be a veterinarily acceptable carrier. Alternatively, the polynucleotide molecule of the vaccine composition can be prepared for oral administration and targeted to the Peyer's patches, such as by microencapsulation, e.g., with poly (lactide-co-glycolide) (PLG), preferably into microparticles of $\leq 10$ um in diameter, as known in the art. See, e.g., Jones et al., 1998, in: Brown and Haaheim (eds.): *Modulation of the Immune Response to Vaccine Antigens*, Dev Biol Stand. Basel, Karger, 92:149–155.

The vaccine composition of the present invention can further comprise a supplemental component selected from the group consisting of an adjuvant, a cytokine, a polynucleotide molecule comprising a nucleotide sequence encoding an immunomodulatory molecule such as a cytokine or carrier protein which can enhance or modulate the immune response against FIV, an agent that facilitates uptake by feline cells of the polynucleotide molecule, such as, e.g., bupivacaine, or a combination thereof. The nucleotide sequence encoding the immunomodulatory molecule can either be situated on the same polynucleotide molecule or expression vector as the nucleotide sequence of the FIV antigen or on a separate polynucleotide molecule or expression vector which is preferably co-administered with, or administered at about the same time as, the polynucleotide molecule comprising the nucleotide sequence of the FIV antigen. The use of DNA vaccines in combination with cytokines, including, e.g., interleukins and interferons, is described in Lee et al., 1999, Vaccine 17:473–479; Okada et al., 1997, J. Immunol. 159:3638–3647; Sin et al., 1997, Vaccine 15:1827–1833; Chow et al., 1997, J. Virol. 71:169–178; Tsuji et al., 1997, J. Immunol. 158:158:4008–4013; and Kim et al., 1997, J. Immunol. 158:816–826, among others, which are incorporated herein by reference.

Adjuvants that can be used in the vaccine of the present invention are those which are compatible with DNA vaccines as known in the art. A non-limiting example of an adjuvant designed for DNA vaccines comprises a negatively charged, mineral-based particle preparation, as described in International Patent Publication WO 98/35562.

The polynucleotide molecules or expression vectors of the vaccine composition can be stored frozen and thawed prior to administration or, more preferably, in lyophilized form and rehydrated prior to administration using a sterile diluent as known in the art.

Polynucleotide molecules and expression vectors of the vaccine composition of the present invention can be microencapsulated to improve administration and efficacy. For example, methods for encapsulating DNA for oral delivery are described in Jones et al., 1998, above.

The present invention further provides a method of vaccinating a cat against FIV, comprising administering to the cat a vaccine composition of the present invention. The vaccine is preferably administered parenterally, e.g., either by subcutaneous, intramuscular or intradermal injection. However, the vaccine may instead be administered by intraperitoneal or intravenous injection, or by other routes, including, e.g., orally, intranasally, rectally, vaginally, intraocularly, or by a combination of routes, and also by delayed release devices as known in the art. The skilled artisan will be able to formulate the vaccine composition according to the route chosen.

An effective dosage of the polynucleotide molecule or expression vector of the present invention can be determined by conventional means, starting with a low dose of the polynucleotide molecule or expression vector, and then increasing the dosage while monitoring the effects. Numerous factors can be taken into consideration when determining an optimal dose per cat. Primary among these is the size, age and general condition of the cat, the presence of other drugs in the cat, the virulence of a particular strain of FIV against which the cat is being vaccinated, and the like. The actual dosage is preferably chosen after consideration of the results from other animal studies.

Vaccine regimens can be selected based on the above-described factors. The vaccine of the invention can be administered at any time during the life of a particular cat depending upon several factors including, e.g., the timing of an outbreak of FIV among other cats. The vaccine can be administered to cats of weaning age or younger, or to more mature animals. Effective protection may require only a primary vaccination, or one or more booster vaccinations may also be needed. A dose that provides adequate protection can be determined empirically by challenging vaccinated and unvaccinated cats (control) with FIV and monitoring and comparing disease progression, including any indicator thereof as known in the art, in the two groups of animals. The timing of vaccination and the number of boosters, if any, will preferably be determined by a veterinarian based on analysis of all relevant factors, some of which are described above.

The concentration of the polynucleotide molecule or expression vector of the present invention in the vaccine preferably ranges from about 0.05 $\mu$g/ml to about 10 mg/ml, and more preferably from about 0.5 $\mu$g/ml to about 5.0 mg/ml. A suitable dosage volume ranges from about 0.1 and 5 ml, which may be administered in a single dose, or in divided doses.

The present invention further provides a kit for vaccinating a cat against FIV, comprising a first container comprising an immunologically effective amount of any one or more of the aforementioned polynucleotide molecules or expression vectors of the present invention. In a non-limiting embodiment, the polynucleotide molecule or expression vector is stored in the first container in lyophilized form. The kit may optionally further comprise a second container comprising a sterile diluent which can be used to dilute or rehydrate the polynucleotide molecule or expression vector in the first container.

5.2. Antibodies

The present invention further provides an isolated antibody that binds specifically to an FIV protein. In a preferred embodiment, the antibody is produced in a mammal in response to administration of a polynucleotide molecule or expression vector having a nucleotide sequence encoding the FIV protein or an epitope thereof, such as, e.g., a polynucleotide molecule or expression vector as present in the vaccine composition of the present invention.

Antibodies can be raised in a host animal in response to administration of the vaccine composition of the present invention or against an expressed or purified FIV antigen, and isolated using known methods. Various host animals, including cats, dogs, pigs, cows, horses, rabbits, goats, sheep, and mice, can be immunized with the vaccine composition of the present invention or with a partially or substantially purified FIV antigen. An adjuvant, such as those listed below in Section 5.3.4, can be selected and used to enhance antibody production. Polyclonal antibodies can be obtained from the serum of the immunized animal, tested for anti-FIV protein specificity, and isolated using standard techniques. Alternatively, monoclonal antibodies against the FIV protein can be prepared and isolated using any technique that provides for the production of antibody molecules by continuous cell lines in culture. These include but are not limited to the hybridoma technique originally described by Kohler and Milstein (Nature, 1975, 256: 495–497); the human B-cell hybridoma technique (Kosbor et al., 1983, Immunology Today 4:72; Cote et al., 1983, Proc. Natl. Acad. Sci. USA 80: 2026–2030); and the EBV-hybridoma technique (Cole et al., 1985, *Monoclonal Antibodies and Cancer Therapy*, Alan R. Liss, Inc., pp. 77–96). Alternatively, techniques described for the production of single chain antibodies (see, e.g., U.S. Pat. No. 4,946,778) can be adapted to produce FIV antigen-specific single chain antibodies. These publications are incorporated herein by reference.

Antibody fragments that contain specific binding sites for an FIV antigen are also encompassed within the present invention, and can be generated and isolated by known techniques. Such fragments include but are not limited to $F(ab')_2$ fragments which can be generated by pepsin digestion of an intact antibody molecule, and Fab fragments which can be generated by reducing the disulfide bridges of the $F(ab')_2$ fragments. Alternatively, Fab expression libraries can be constructed (Huse et al., 1989, Science 246: 1275–1281) to allow rapid identification of Fab fragments having the desired specificity to the FIV antigen.

Techniques for the production and isolation of monoclonal antibodies and antibody fragments are well-known in the art, and are additionally described, among other places, in Harlow and Lane, 1988, *Antibodies: A Laboratory Manual*, Cold Spring Harbor Laboratory, and in J. W. Goding, 1986, *Monoclonal Antibodies: Principles and Practice*, Academic Press, London, which are incorporated herein by reference.

5.3. FIV Protein-based Vaccines

The present invention further provides a vaccine composition against FIV, comprising an immunologically effective amount of a GAG protein, POL protein, ENV protein, regulatory protein, or a combination thereof, from an FIV strain. The FIV strain can be any strain of FIV, but is preferably strain FIV-141. The GAG protein is selected from the group consisting of the GAG polyprotein and its substituent proteins, i.e., MA, CA and NC. The POL protein is selected from the group consisting of the POL polyprotein and its substituent proteins, i.e., PR, RT, DU and IN. The ENV protein is selected from the group consisting of the ENV polyprotein and its substituent proteins, i.e., SU and TM. The regulatory protein is selected from the group consisting of Rev, Vif and ORF2.

In a more preferred embodiment, the vaccine composition of the present invention comprises a combination of FIV proteins. In a preferred embodiment, the proteins of the vaccine composition comprise at least two different FIV proteins selected from among the FIV structural and FIV non-structural proteins. In a further preferred embodiment, the proteins of the vaccine composition comprise at least two different GAG proteins from FIV. In a further preferred embodiment, the proteins of the vaccine composition comprise at least one FIV structural protein and at least one FIV non-structural protein. In a further preferred embodiment, the proteins of the vaccine composition comprise at least three different FIV proteins selected from among the FIV structural and FIV non-structural proteins. In a further preferred embodiment, the proteins of the vaccine composition comprise at least four different FIV proteins selected from among the FIV structural and FIV non-structural proteins. In a further preferred embodiment, the proteins of the vaccine composition comprise at least five different FIV proteins selected from among the FIV structural and FIV non-structural proteins. In a further preferred embodiment, the proteins of the vaccine composition comprise at least six different FIV proteins selected from among the FIV structural and FIV non-structural proteins. In a further preferred embodiment, the proteins of the vaccine composition comprise at least seven different FIV proteins selected from among the FIV structural and FIV non-structural proteins.

In a particularly preferred embodiment, the combination of FIV proteins is selected from the group consisting of GAG/MA/CA/NC; GAG/ENV; GAG/MA/CA/NC/ENV/SU/TM; MA/CA/NC; GAG/MA/NC/DU/PR; and MA/CA/NC/SU/TM.

The vaccine composition can alternatively comprise: (a) at least one polypeptide which is homologous to any of the aforementioned FIV proteins; (b) at least one peptide fragment of any of the aforementioned FIV proteins, or homologous polypeptides of (a); (c) at least one fusion protein comprising any of the aforementioned FIV proteins, homologous polypeptides of (a) or peptide fragments of (b) fused to a fusion partner; (d) at least one of an analog or derivative of any of the aforementioned FIV proteins, homologous polypeptides of (a), peptide fragments of (b), or fusion proteins of (c); or (e) a combination thereof.

As used herein, the term "homologous" refers to a polypeptide otherwise having the amino acid sequence of an FIV protein or polypeptide, but in which one or more amino acid residues have been conservatively substituted with a different amino acid residue as defined above in Section 5.1.1, where the resulting polypeptide is useful in practicing the present invention as usefulness is defined therein. In a preferred embodiment, such a polypeptide has at least about 70%, more preferably at least about 80%, and most preferably at least about 90% sequence identity to a native FIV protein or polypeptide.

As used herein, a "peptide fragment" of an FIV protein refers to a polypeptide consisting of less than the complete amino acid sequence of the corresponding full-length FIV protein, but comprising a sub-sequence of at least about 10 amino acid residues, more preferably at least about 20 amino acid residues, and most preferably at least about 30 amino acid residues of the amino acid sequence thereof, and that is useful in practicing the present invention as defined above. In a preferred embodiment, a peptide fragment of an FIV protein comprises the amino acid sequence of an epitope of the FIV protein against which antibodies can be raised.

As used herein, a "fusion protein" comprises an FIV protein, homologous polypeptide or peptide fragment of the present invention joined to a carrier or fusion partner, which fusion protein is useful in practicing the present invention, as usefulness is defined above for polypeptides. See Section 5.3.1 below for examples of fusion partners. Fusion proteins are useful for a variety of reasons, including to increase the stability of recombinantly-expressed FIV polypeptides, as distinct antigenic components in an FIV vaccine, to enhance the induction of antisera against the particular FIV antigen partner, to study the biochemical properties of the FIV antigen partner, to serve as diagnostic reagents, or to aid in the identification or purification of the expressed FIV antigen partner as described below.

Fusion proteins of the present invention can be engineered using standard techniques to further contain specific protease cleavage sites so that the particular FIV antigen partner can be released from the carrier or fusion partner by treatment with a specific protease. For example, a fusion protein of the present invention can further comprise a thrombin or factor Xa cleavage site, among others.

The present invention further provides analogs and derivatives of an FIV protein, homologous polypeptide, peptide fragment or fusion protein, where such analogs and derivatives are useful in practicing the present invention, as usefulness is defined above for polypeptides. Manipulations that result in the production of analogs can be carried out either at the gene level or at the protein level, or both, to improve or otherwise alter the biological or immunological characteristics of the particular polypeptide from which the analog is prepared. For example, at the gene level, a cloned DNA molecule encoding an FIV protein can be modified by one or more known strategies to encode an analog of that protein. Such modifications include, but are not limited to, endonuclease digestion, and mutations that create or destroy translation, initiation or termination sequences, or that create variations in the coding region, or a combination thereof. Such techniques are described, among other places, in Maniatis et al., 1989, above; Ausubel et al., 1989, above; Sambrook et al., 1989, above; Innis et al. (eds), 1995, above; and Erlich (ed), 1992, above.

Alternatively or additionally, an analog of the present invention can be prepared by modification of an FIV protein or other polypeptide of the present invention at the protein level. Chemical modifications of the protein can be carried out using known techniques, including but not limited to one or more of the following: substitution of one or more L-amino acids of the protein with corresponding D-amino acids, amino acid analogs, or amino acid mimics, so as to produce, e.g., carbazates or tertiary centers; or specific chemical modification, such as proteolytic cleavage with, e.g., trypsin, chymotrypsin, papain or V8 protease, or treatment with $NaBH_4$ or cyanogen bromide, or acetylation, formylation, oxidation or reduction, etc.

An FIV protein or other polypeptide of the present invention can be derivatized by conjugation thereto of one or more chemical groups, including but not limited to acetyl groups, sulfur bridging groups, glycosyl groups, lipids, and phosphates, and/or a second FIV protein or other polypeptide of the present invention, or another protein, such as, e.g., serum albumin, keyhole limpet hemocyanin, or commercially activated BSA, or a polyamino acid (e.g., polylysine), or a polysaccharide, (e.g., sepharose, agarose, or modified or unmodified celluloses), among others. Such conjugation is preferably by covalent linkage at amino acid side chains and/or at the N-terminus or C-terminus of the FIV protein. Methods for carrying out such conjugation reactions are well known in the field of protein chemistry.

Derivatives useful in practicing the claimed invention also include those in which a water-soluble polymer, such as, e.g., polyethylene glycol, is conjugated to an FIV protein or other polypeptide of the present invention, or to an analog thereof, thereby providing additional desirable properties while retaining, at least in part, or improving the immunogenicity of the FIV protein. These additional desirable properties include, e.g., increased solubility in aqueous solutions, increased stability in storage, increased resistance to proteolytic degradation, and increased in vivo half-life. Water-soluble polymers suitable for conjugation to an FIV protein or other polypeptide of the present invention include but are not limited to polyethylene glycol homopolymers, polypropylene glycol homopolymers, copolymers of ethylene glycol with propylene glycol, wherein said homopolymers and copolymers are unsubstituted or substituted at one end with an alkyl group, polyoxyethylated polyols, polyvinyl alcohol, polysaccharides, polyvinyl ethyl ethers, and $\alpha,\beta$-poly[2-hydroxyethyl]-DL-aspartamide. Polyethylene glycol is particularly preferred. Methods for making water-soluble polymer conjugates of polypeptides are known in the art and are described in, among other places, U.S. Pat. No. 3,788,948; U.S. Pat. No. 3,960,830; U.S. Pat. No. 4,002,531; U.S. Pat. No. 4,055,635; U.S. Pat. No. 4,179,337; U.S. Pat. No. 4,261,973; U.S. Pat. No. 4,412,989; U.S. Pat. No. 4,414,147; U.S. Pat. No. 4,415,665; U.S. Pat. No. 4,609,546; U.S. Pat. No. 4,732,863; U.S. Pat. No. 4,745,180; European Patent (EP) 152,847; EP 98,110; and Japanese Patent (JP) 5,792,435, which patents are incorporated herein by reference.

5.3.1. Recombinant Vectors

Protein-based FIV vaccines of the present invention can be prepared by recombinant expression of a polynucleotide molecule having a nucleotide sequences encoding a particular FIV protein or polypeptide. To carry out such expression, the present invention provides recombinant cloning and expression vectors comprising the polynucleotide molecule. Expression vectors of the present invention are preferably constructed so that the polynucleotide molecule is in operative association with one or more regulatory elements necessary for transcription and translation. Such expression vectors are useful in an expression system, such as a transformed host cell, to produce a recombinantly-expressed FIV protein. More preferably, expression vectors of the present invention are constructed so that the polynucleotide molecule is in operative association with one or more regulatory elements necessary for transcription and translation in a bacterial cell, or in a mammalian host cell such as a feline cell. In addition to serving as a reagent for the production of an FIV protein in vitro, an expression vector capable of expression in a feline cell is also useful as a vaccinal agent in a DNA vaccine composition for administration to cats as described above.

As used herein, the term "regulatory element" includes but is not limited to nucleotide sequences that encode inducible and non-inducible promoters, enhancers, operators, and other elements known in the art that can serve to drive and/or regulate expression of the coding sequence of the polynucleotide molecule. As used herein, the polynucleotide molecule is in "operative association" with one or more regulatory elements where the regulatory elements effectively regulate and provide for the transcription of the coding sequence of the polynucleotide molecule, or the translation of its mRNA, or both.

A variety of expression vectors are known in the art that can be utilized to express the coding sequence of a polynucleotide molecule of the present invention, including recombinant bacteriophage DNA, plasmid DNA and cosmid DNA expression vectors containing the polynucleotide molecule, for transformation of bacteria or yeast; and recombinant virus expression vectors such as, e.g., baculovirus containing the polynucleotide molecule for transfection of insect cells, or adenovirus or vaccinia virus containing the polynucleotide molecule for transfection of mammalian cells, among others.

Typical prokaryotic expression vector plasmids that can be engineered to contain a polynucleotide molecule of the present invention include pUC8, pUC9, pBR322 and pBR329 (Biorad Laboratories, Richmond, Calif.), and pPL and pKK223 (Pharmacia, Piscataway, N.J.), among many others.

Typical eukaryotic expression vectors that can be engineered to contain a polynucleotide molecule according to the present invention include an ecdysone-inducible mammalian expression system (Invitrogen, Carlsbad, Calif.), cytomegalovirus promoter-enhancer-based systems (Promega, Madison, Wis.; Stratagene, La Jolla, Calif.; Invitrogen), and baculovirus-based expression systems (Promega), among others.

The regulatory elements of these and other vectors can vary in their strength and specificities. Depending on the host/vector system utilized, any of a number of suitable transcription and translation elements can be used. For instance, when cloning in mammalian cell systems, promoters isolated from the genome of mammalian cells, e.g., mouse metallothionein promoter, or from viruses that grow in these cells, e.g., vaccinia virus 7.5K promoter or Moloney murine sarcoma virus long terminal repeat, may be used. Promoters obtained by recombinant DNA or synthetic techniques may also be used to provide for transcription of the inserted sequence. In addition, expression from certain promoters can be elevated in the presence of particular inducers, e.g., zinc and cadmium ions for metallothionein promoters.

Non-limiting examples of transcriptional regulatory regions or promoters include for bacteria, the β-gal promoter, the T7 promoter, the TAC promoter, λ left and right promoters, trp and lac promoters, and trp-lac fusion promoters; for yeast, glycolytic enzyme promoters, such as ADH-I and -II promoters, GPK promoter, PGI promoter, and TRP promoter; for mammalian cells, SV40 early and late promoters, and adenovirus major late promoters.

Specific initiation signals are also required for sufficient translation of inserted FIV coding sequences. These signals typically include an ATG initiation codon and adjacent sequences. In cases where a polynucleotide molecule, including its own initiation codon and adjacent sequences, is inserted into an appropriate expression vector, no additional translation control signals may be needed. However, in cases where only a portion of a coding sequence is inserted, exogenous translational control signals, including an ATG initiation codon, and a translation stop codon such as TAA, TAG, or TGA, may be required. These exogenous translational control signals and initiation codons can be obtained from a variety of sources, both natural and synthetic. Furthermore, the initiation codon must be in phase with the reading frame of the coding region to ensure in-frame translation of the entire insert.

The polynucleotide molecule of the expression vector may further comprise a nucleotide sequence which encodes an additional polypeptide fused to the FIV antigen. Such an additional polypeptide can be an immunomodulatory molecule such as a cytokine useful to enhance or otherwise modulate the immune response of a cat to which the expression vector or encoded fusion protein has been administered. The use of DNA vaccines with cytokines, including, e.g., interleukins and interferons, is presented in Lee et al., 1999, above; Okada et al., 1997, above; Sin et al., 1997, above; Chow et al., 1997, above; Tsuji et at., 1997, above; and Kim et al., 1997, above, among others.

Additional fusion protein expression vectors include vectors incorporating sequences that encode β-galactosidase and trpE fusions, maltose-binding protein fusions, glutathione-S-transferase fusions and polyhistidine fusions (carrier regions). Such fusion proteins can be useful to aid in purification of the expressed protein. For example, an FIV antigen-maltose-binding protein fusion can be purified using amylose resin; an FIV antigen-glutathione-S-transferase fusion protein can be purified using glutathione-agarose beads; and an FIV antigen-polyhistidine fusion can be purified using divalent nickel resin. Alternatively, antibodies against a carrier protein or peptide can be used for affinity chromatography purification of the fusion protein. For example, a nucleotide sequence coding for the target epitope of a monoclonal antibody can be engineered into the expression vector in operative association with the regulatory elements and situated so that the expressed epitope is fused to the FIV antigen. For example, a nucleotide sequence coding for the FLAG™ epitope tag (International Biotechnologies Inc.), which is a hydrophilic marker peptide, can be inserted by standard techniques into the expression vector at a point corresponding, e.g., to the amino or carboxyl terminus of the FIV antigen. The expressed FIV antigen-FLAG™ epitope fusion product can then be detected and affinity-purified using commercially available anti-FLAG™ antibodies. In an alternative embodiment, the FIV protein or other polypeptide is fused to an epitope tag from human influenza hemagglutinin, such as a nine amino acid epitope tag from human influenza hemagglutinin (HA) protein as described below in Section 6.4.

The expression vector can also be engineered to contain polylinker sequences that encode specific protease cleavage sites so that the expressed FIV antigen can be released from the carrier region or fusion partner by treatment with a specific protease. For example, the fusion protein vector can include DNA sequences encoding thrombin or factor Xa cleavage sites, among others.

A signal sequence upstream from and in reading frame with the FIV antigen coding region can be engineered into the expression vector by known methods to direct the trafficking and secretion of the expressed protein. Non-limiting examples of signal sequences include those from α-factor, immunoglobulins, outer membrane proteins, penicillinase, and T-cell receptors, among others.

To aid in the selection of host cells transformed or transfected with an expression vector of the present invention, the expression vector can be engineered to further comprise a coding sequence for a reporter gene product or other selectable marker. Such a coding sequence is preferably in operative association with the regulatory element coding sequences, as described above. Reporter genes that are useful in the invention are well known in the art and include those encoding chloramphenicol acetyltransferase (CAT), green fluorescent protein, firefly luciferase, and human growth hormone, among others. Selectable markers, and their nucleotide sequences, are well-known in the art, and include gene products conferring resistance to antibiotics or anti-metabolites, or that supply an auxotrophic requirement. Examples of such sequences include those that encode thymidine kinase activity, or resistance to erythromycin, ampicillin, or kanamycin, among others.

Methods are well-known in the art for constructing expression vectors containing particular coding sequences in operative association with appropriate regulatory elements, as well as nucleotide sequences encoding selectable markers, signal sequences, and fusion partners, and such methods may be used to practice the present invention. Such methods include in vitro recombinant techniques, synthetic techniques, and in vivo genetic recombination, as described, among other places, in Maniatis et al., 1989, above; Ausubel et al., 1989, above; and Sambrook et al., 1989, above.

5.3.2. Transformation of Host Cells

Expression vectors comprising a polynucleotide molecule of interest can be transformed into host cells for propagation, or for expression of the encoded FIV antigen. Host cells useful in the practice of the invention can be eukaryotic or prokaryotic. Such transformed host cells include but are not limited to microorganisms, such as bacteria transformed with recombinant bacteriophage DNA, plasmid DNA or cosmid DNA expression vectors; or yeast transformed with a recombinant expression vector; or animal cells, such as insect cells infected with a recombinant virus expression vector, e.g., baculovirus, or mammalian cells, such as feline cells, infected with a recombinant virus expression vector, e.g., adenovirus or vaccinia virus, among others.

Bacterial cells for use as host cells include a strain of $E.$ $coli$ such as, e.g., the DH5α strain, available from the ATCC, Rockville, Md., USA (Accession No. 31343), or from Stratagene (La Jolla, Calif.). Eukaryotic host cells include yeast cells, although mammalian cells, such as from a cat, mouse, hamster, cow, monkey, or human cell line, may also be used effectively. Specific examples of eukaryotic host cells that may be used to express the recombinant protein of the invention include Chinese hamster ovary (CHO) cells (e.g., ATCC Accession No. CCL-61), NIH Swiss mouse embryo cells NIH/3T3 (e.g., ATCC Accession No. CRL-1658), Madin-Darby bovine kidney (MDBK) cells (ATCC Accession No. CCL-22), and thymidine kinase-deficient cells, e.g., L-M (TK$^-$) (ATCC Accession No. CCL-1.3) and tk$^-$-ts13 (ATCC Accession No. CRL-1632).

The recombinant expression vector of the invention is preferably transformed or transfected into one or more host cells of a substantially homogeneous culture of cells. The expression vector is generally introduced into host cells in accordance with known techniques, such as, e.g., by calcium phosphate precipitation, calcium chloride treatment, microinjection, electroporation, transfection by contact with a recombined virus, liposome-mediated transfection, DEAE-dextran transfection, transduction, conjugation, or microprojectile bombardment, among others. Selection of transformants may be conducted by standard procedures, such as by selecting for cells expressing a selectable marker, e.g., antibiotic resistance, associated with the recombinant expression vector.

Once the expression vector is introduced into the host cell, the integration and maintenance of the polynucleotide molecule of the present invention, either in the host cell genome or episomally, can be confirmed by standard techniques, e.g., by Southern hybridization analysis, restriction enzyme analysis, PCR analysis including reverse transcriptase PCR (RT-PCR), or by immunological assay to detect the expected protein product. Host cells containing and/or expressing the polynucleotide molecule of the present invention may be identified by any of at least four general approaches, which are well-known in the art, including: (i) DNA-DNA, DNA-RNA, or RNA-antisense RNA hybridization; (ii) detecting the presence of "marker" gene functions; (iii) assessing the level of transcription as measured by the expression, e.g., of an FIV-specific mRNA transcript in the host cell; or (iv) detecting the presence of mature polypeptide product, e.g., by immunoassay, as known in the art.

5.3.3. Expression and Purification of Recombinant Polypeptides

Once a polynucleotide molecule of interest has been stably introduced into an appropriate host cell, the transformed host cell can be clonally propagated, and the resulting cells grown under conditions conducive to the maximum production of the encoded FIV antigen. Such conditions typically include growing transformed cells to high density. Where the expression vector comprises an inducible promoter, appropriate induction conditions such as, e.g., temperature shift, exhaustion of nutrients, addition of gratuitous inducers (e.g., analogs of carbohydrates, such as isopropyl-β-D-thiogalactopyranoside (IPTG)), accumulation of excess metabolic by-products, or the like, are employed as needed to induce expression.

Where the expressed FIV antigen is retained inside the host cells, the cells are harvested and lysed, and the product purified from the lysate under extraction conditions known in the art to minimize protein degradation such as, e.g., at 4° C., or in the presence of protease inhibitors, or both. Where the expressed FIV antigen is secreted from the host cells, the exhausted nutrient medium may simply be collected and the protein isolated therefrom.

The expressed FIV antigen can be purified from cell lysates or culture medium, as appropriate, using standard methods, including but not limited to one or more of the following methods: ammonium sulfate precipitation, size fractionation, ion exchange chromatography, HPLC, density centrifugation, and affinity chromatography. Where the expressed FIV antigen exhibits enzymatic activity, increasing purity of the preparation can be monitored at each step of the purification procedure by use of an appropriate enzyme assay, as known in the art. If the expressed protein lacks biological activity, it may be detected as based, e.g., on size, or reactivity with an antibody otherwise specific for the FIV antigen, or by the presence of a fusion tag.

5.3.4. Protein Vaccine Formulation and Use

The present invention provides a method of preparing a vaccine composition against FIV, comprising combining an immunologically effective amount of any of the aforementioned FIV-related proteins or polypeptides, or a combination thereof, with a veterinarily acceptable carrier in a form suitable for administration to a cat. Alternatively, any one or more of the aforementioned proteins or polypeptides can be combined with any one or more of the aforementioned polynucleotide molecules or expression vectors of the present invention, and a veterinarily acceptable carrier, to prepare a combined DNA/protein vaccine composition.

As used herein to refer to proteins and polypeptides, the term "immunologically effective amount" refers to that amount of protein or polypeptide antigen capable of inducing, or enhancing the induction of, a protective response against FIV when administered to a cat after either a single administration, or after multiple administrations.

The phrases "capable of inducing a protective response" and "can enhance the induction of a protective immune response against FIV", as well as the terms "protective response" and "protect", and the like, as used herein are as defined above in Section 5.1.2.

The vaccine composition of the present invention will typically be adapted for parenteral administration, e.g., by intradermal or intramuscular injection, although other routes (e.g., intravenous, intranasal, oral, etc.) can also be effective. Vaccine compositions of the present invention can be formulated following accepted convention using standard buffers, carriers, stabilizers, diluents, preservatives, and solubilizers, and can also be formulated to facilitate sustained release. Diluents can include water, saline, dextrose, ethanol, glycerol, and the like. Additives for isotonicity can include sodium chloride, dextrose, mannitol, sorbitol, and lactose, among others. Stabilizers include albumin, among others.

Adjuvants can optionally be employed in the vaccine. Non-limiting examples of adjuvants include the RIBI adjuvant system (Ribi Inc.), alum, aluminum hydroxide gel, oil-in-water emulsions, water-in-oil emulsions such as, e.g., Freund's complete and incomplete adjuvants, Block co polymer (CytRx, Atlanta Ga.), SAF-M (Chiron, Emeryville Calif.), AMPHIGEN® adjuvant, saponin, Quil A, QS-21 (Cambridge Biotech Inc., Cambridge Mass.), or other saponin fractions, SEAM-1, monophosphoryl lipid A, Avridine lipid-amine adjuvant, heat-labile enterotoxin from *E. coli* (recombinant or otherwise), cholera toxin, or muramyl dipeptide, among many others. The vaccine can further comprise one or more other immunomodulatory agents such as, e.g., interleukins, interferons, or other cytokines, or a polynucleotide molecule having a nucleotide sequence encoding the same.

Suitable veterinarily acceptable vaccine vehicles, carriers, and additives are known, or will be apparent to those skilled in the art; see, e.g., Remington's *Pharmaceutical Science*, 18th Ed., 1990, Mack Publishing, which is incorporated herein by reference. The vaccine can be stored in solution, or alternatively in lyophilized form to be reconstituted with a sterile diluent solution prior to administration.

The present invention further provides vaccine formulations for the sustained release of the antigen. Examples of such sustained release formulations include the proteins or polypeptides of the present invention in combination with composites of biocompatible polymers, such as, e.g., poly (lactic acid), poly(lactic-co-glycolic acid), methylcellulose, hyaluronic acid, collagen and the like. The structure, selection and use of degradable polymers in drug delivery vehicles have been reviewed in several publications, including A. Domb et al., 1992, Polymers for Advanced Technologies 3: 279–292, which is incorporated herein by reference. Additional guidance in selecting and using polymers in pharmaceutical formulations can be found in the text by M. Chasin and R. Langer (eds), 1990, "Biodegradable Polymers as Drug Delivery Systems" in: *Drugs and the Pharmaceutical Sciences*, Vol. 45, M. Dekker, New York, which is also incorporated herein by reference. Liposomes and liposome derivatives (e.g., cochleates, vesicles) can also be used to provide for the sustained release of the antigen. In addition, methods for microencapsulating antigens are well-known in the art, and include techniques described, e.g., in U.S. Pat. No. 3,137,631; U.S. Pat. No. 3,959,457; U.S. Pat. 4,205,060; U.S. Pat. No. 4,606,940; U.S. Pat. No. 4,744,933; U.S. Pat. No. 5,132,117; and International Patent Publication WO 95/28227, all of which are incorporated herein by reference.

In a non-limiting embodiment, the vaccine of the present invention can be a combination vaccine for protecting cats against FIV and, optionally, one or more other diseases or pathological conditions that can afflict felines, which combination vaccine comprises a first component comprising an immunologically effective amount of an antigen of the present invention selected from the group consisting of an FIV-related polynucleotide, protein or polypeptide as described above; a second component comprising an immunologically effective amount of an antigen that is different from the antigen in the first component, and which is capable of inducing or enhancing the induction of a protective response against a disease or pathological condition that afflict cats; and a veterinarily acceptable carrier.

The second component of the combination vaccine is selected based on its ability to either induce or enhance the induction of a protective response against either FIV or another pathogen, disease, or pathological condition that afflicts cats, as known in the art, where the definition of the ability to induce or enhance the induction of a protective response generally follows the definitions provided above as directed to FIV, or as applied in parallel fashion to the other pathogen, disease or pathological condition being treated, as appropriate. Any immunogenic composition now known or to be determined in the future to be useful in a vaccine composition for cats can be used as the second component of the combination vaccine. Such immunogenic compositions include but are not limited to those that induce or enhance the induction of a protective response against feline leukemia virus, feline herpes virus, feline calicivirus, or feline coronavirus, among others.

The antigen of the second component can optionally be covalently linked to the antigen of the first component to produce a chimeric molecule. In a non-limiting embodiment, the antigen of the second component comprises a hapten, the immunogenicity of which is detectably increased by conjugation to the antigen of the first component. Chimeric molecules comprising covalently linked antigens of the first and second components of the combination vaccine can be synthesized using one or more techniques known in the art. For example, a chimeric molecule can be produced synthetically using a commercially available peptide synthesizer utilizing standard chemical synthetic processes (see, e.g., Merrifield, 1985, Science 232:341–347). Alternatively, the separate antigens can be separately synthesized and then linked together by the use of chemical linking groups, as known in the art. Alternatively, a chimeric molecule can be produced using recombinant DNA technology whereby, e.g., separate polynucleotide molecules having sequences encoding the different antigens of the chimeric molecule are spliced together in-frame and expressed in a suitable transformed host cell for subsequent isolation of the chimeric fusion polypeptide. Where the vaccine of the invention is a DNA vaccine, the spliced polynucleotide molecule can itself be used in the vaccine composition, preferably in the form of an expression vector. Ample guidance for carrying out such recombinant techniques is provided, among other places, in Maniatis et al., 1989, above; Ausubel et al., 1989, above; Sambrook et al., 1989, above; Innis et al., 1995, above; and Erlich, 1992, above.

The present invention further provides a method of preparing a vaccine for protecting cats against FIV, comprising combining an immunologically effective amount of one or more antigens of the present invention selected from the group consisting of an FIV protein, homologous polypeptide, peptide fragment, fusion protein, analog and derivative, with a veterinarily acceptable carrier or diluent, in a form suitable for administration to cats.

The present invention further provides a method of vaccinating cats against FIV, comprising administering a vaccine composition comprising an immunologically effective amount of one or more antigens of the present invention selected from the group consisting of an FIV protein, homologous polypeptide, peptide fragment, fusion protein, analog and derivative of the present invention to a cat. The amount of FIV-related antigen administered will preferably range from about 0.1 μg to about 10 mg of polypeptide, more preferably from about 10 μg to about 1 mg, and most preferably from about 25 μg to about 0.1 mg. In addition, the typical dose volume of the vaccine will range from about 0.5 ml to about 5 ml per dose per animal.

Vaccine regimens can be determined as described above. The vaccine can be administered in a single dose or in divided doses by any appropriate route such as, e.g., by oral, intranasal, intramuscular, intra-lymph node, intradermal, intraperitoneal, subcutaneous, rectal or vaginal administration, or by a combination of routes. The skilled artisan will readily be able to formulate the vaccine composition according to the route chosen. The timing of vaccination and the number of boosters, if any, will preferably be determined by a veterinarian based on analysis of all relevant factors, some of which are described above.

5.4. Oligonucleotide Molecules

The nucleotide sequences of the polynucleotide molecules disclosed herein provide the information necessary to construct oligonucleotide molecules that can be used as amplification primers and as probes in differential disease diagnosis, and these can readily be designed by the skilled artisan in light of this disclosure. Such oligonucleotide molecules are preferably at least about 15 nucleotides in length. Amplification of specific FIV genes and nucleotide sequences can be carried out using such suitably designed oligonucleotides by applying standard techniques such as, e.g., the polymerase chain reaction (PCR) which is described, among other places, in Innis et al. (eds), 1995, above; and Erlich (ed), 1992, above. In a preferred embodiment, such oligonucleotide molecules comprise nucleotide sequences selected from the group consisting of SEQ ID NOS: 2 to 49, or the complements of said sequences.

Regarding diagnostics, oligonucleotide molecules of the present invention can be used in a standard amplification procedure to detect the presence of an FIV polynucleotide molecule in a sample of feline tissue or fluid, such as brain tissue, lung tissue, placental tissue, blood, cerebrospinal fluid, mucous, urine, amniotic fluid, etc. The production of a specific amplification product can be used to support a diagnosis of FIV infection, while lack of an amplified product may point to a lack of infection.

Generally, for PCR amplification, a mixture comprising suitably designed primers, a template comprising the nucleotide sequence to be amplified, and appropriate PCR enzymes and buffers, is prepared and processed according to standard protocols to amplify a specific FIV polynucleotide molecule of the template or a portion thereof. Other amplification techniques known in the art, e.g., the ligase chain reaction, may alternatively be used.

The following examples are illustrative only, and are not intended to limit the scope of the present invention.

6. EXAMPLE

CLONING of the FIV PROVIRAL GENOME and INDIVIDUAL GENES INTO EUKARYOTIC EXPRESSION VECTORS

6.1. Viral and Proviral DNA Isolation

Peripheral blood was obtained from a 5 yr old male cat prior to euthanasia at the Capital Humane Society, Lincoln, Nebr. The plasma sample tested FIV positive and FeLV negative (FIV antibody and FeLV antigen kits, IDEXX, Westbrook, Me., USA), and the strain of FIV was designated as FIV-141. The source FIV plasma sample was sterile-filtered (0.22 μM) and inoculated intravenously into an 8 wk old SPF cat (identification No. 96QGW2), which was then observed for 12 weeks. Peripheral blood samples were taken weekly. Tissue samples taken at necropsy were used to confirm FIV infection, and to re-isolate and characterize the molecular and biological features of the new FIV isolate. Feline genomic DNA was isolated from the spleen of the FIV-inoculated SPF cat using a genomic DNA extraction kit (Stratagene, La Jolla, Calif.), and purified genomic DNA was dissolved in TE buffer at a concentration of 1 μg/μl and stored at −70° C.

6.2. Initial PCR Amplification and Cloning of Three Segments of the FIV-141 Genome Three sets of oligonucleotides were designed based upon the published sequences of other FIV isolates (Talbott et al., 1989, Proc. Natl. Acad. Sci. USA, 86:5743–5747; Miyazawa et al., 1991, J. Virol. 65:1572–1577; Talbott et al., 1990, J. Virol. 64:4605–4613). These oligonucleotides were used to amplify three segments of the FIV-141 genome, the first segment at the 5' end, the second segment at the 3' end, and the third segment in the middle of the genome. Because of a low copy number of the FIV proviral genome in infected tissue, two rounds of PCR amplification were performed using a semi-nested set of primers for each segment.

Three primers, designated as Pr-1 (SEQ ID NO:2), Pr-2 (SEQ ID NO:3) and Pr-8 (SEQ ID NO:8), were used to amplify the 5' segment of the FIV-141 proviral genome comprising nucleotides 117 to 646 of SEQ ID NO:1. This segment spans the majority of the 5' LTR, the intervening sequence between the 5' LTR and the GAG open reading frame, and the N-terminal portion of the GAG gene. Primer sequences are presented in TABLE 1 below. The first round PCR amplification was performed using 200 ng each of Pr-1 (SEQ ID NO:2) and Pr-8 (SEQ ID NO:8) as primers, and 1 μg of feline genomic DNA as template, with a mixture of 0.5 U Taq DNA polymerase (Gibco BRL, Gaithersburg, Md.) and 1 U Pfu DNA polymerase (Stratagene, La Jolla, Calif.). PCR amplification conditions were: 94° C., 1 min; followed by 30 cycles of denaturing at 94° C. for 45 sec, annealing at 52° C. for 45 sec, and extension at 72° C. for 2 min. The second round PCR amplification was performed using primers Pr-1 (SEQ ID NO:2) and Pr-2 (SEQ ID NO:3) (TABLE 1) and 2 μl of the first round PCR products as template. The same conditions as the first round amplification were used except that the annealing temperature was 55° C.

Three primers, Pr-5 (SEQ ID NO:5), Pr-6 (SEQ ID NO:6) and Pr-7 (SEQ ID NO:7) (TABLE 1), were used to perform two rounds of PCR amplifications and clone the 3' segment of the FIV-141 proviral genome. The 3' segment spans nucleotides 8874 to 9367 of SEQ ID NO:1, consisting of the intervening sequence between the 3' LTR and the ENV gene, and most of the 3' LTR. Pr-5 (SEQ ID NO:5) and Pr-6 (SEQ ID NO:6) were used in the first round, while Pr-6 (SEQ ID NO:6) and Pr-7 (SEQ ID NO:7) were used for the second round PCR amplification. The same conditions were applied to the reaction and amplification in the first and second rounds as described above.

Three primers, Pr-3 (SEQ ID NO:4), Pr-9 (SEQ ID NO:9) and Pr-10 (SEQ ID NO:10) (TABLE 1), were designed to amplify the segment from nucleotides 5147 to 5631 of SEQ ID NO:1, spanning the C-terminal portion of the IN gene and the N-terminal portion of the Vif gene. The first round amplification was performed using Pr-3 (SEQ ID NO:4) and Pr-10 (SEQ ID NO:10), followed by the second round amplification using Pr-9 (SEQ ID NO:9) and Pr-10 (SEQ ID NO:10). The same conditions were applied to the reaction and amplification in the first and second rounds as described above.

PCR products from each of the three second round amplifications were applied to a 1% agarose gel and the expected size bands for all three regions were purified (Wizard PCR Preps kit; Promega, Madison, Wis.). The purified PCR fragments were cloned into pCR-Script Amp SK(+) vector (Stratagene, La Jolla, Calif.) according to manufacturer's instructions, and their presence was confirmed by restriction enzyme digestion. The FIV specific sequence of each clone was determined by sequencing the two strands of the plasmid DNA (Advanced Genetic Analysis Center, St. Paul, Minn.). The consensus sequence from three independent clones was used to define the authentic FIV-141 sequence.

reaction was set up in a total volume of 50 μl, containing 1 μl of feline genomic DNA template (1 μg/μl), 1 μl of each primer (100 ng/μl), 5 μl of 10×Advantage Tth PCR reaction buffer (Advantage Genomic PCR Kit; Clontech, Palo Alto, Calif.), 2.2 μl of 25 mM Mg(Oac)$_2$, 1 μl of 50×dNTP mix (10 mM each), 1 μl of 50×Advantage Tth Polymerase mix, 1 μl of Pfu polymerase (2.5 U/μl), and 36.8 μl of sterile water. The reaction mix was heated at 94° C. for 2 min, followed by 30 cycles of amplification; 94° C. for 30 sec and 68° C. for 6 min. The second round PCR amplification was carried out using 2 μl of the first round PCR product as template and primers Pr-11 (SEQ ID NO:11) and Pr-12 (SEQ ID NO:12) (TABLE 1). To facilitate the later construction of a full-length FIV-141 clone, an Mlu I restriction site was incorporated into primer Pr-12 (SEQ ID NO:12) by a silent mutation. The Mlu I site is underlined in the Pr-12 (SEQ ID NO:12) primer sequence (TABLE 1). The same PCR conditions were used in the second round. After two PCR amplification rounds, a 5460 bp fragment was obtained.

To clone the 3' half of the proviral genome of FIV-141, three primers, Pr-9 (SEQ ID NO:9), Pr-13 (SEQ ID NO:13)

TABLE 1

Primers used for cloning the FIV-141 proviral genome from infected cat spleen genomic DNA

| Primer (SEQ ID NO:) | Direction | Sequence |
| --- | --- | --- |
| Pr-1 (2)  | forward | 117-CCGCAAAACCACATCCTATGTAAAGCTTGC-146 |
| Pr-2 (3)  | reverse | 646-CGCCCCTGTCCATTCCCCATGTTGCTGTAG-617 |
| Pr-3 (4)  | forward | 4738-ACAAACAGATAATGGACCAAATTTTAAAAA-4767 |
| Pr-5 (5)  | forward | 8793-GCAATGTGGCATGTCTGAAAAAGAGGAGGA-8822 |
| Pr-6 (6)  | reverse | 9367-TCTGTGGGAGCCTCAAGGGAGAACTC-9342 |
| Pr-7 (7)  | forward | 8874-TCTTCCCTTTGAGGAAGATATGTCATATGAATCC-8907 |
| Pr-8 (8)  | reverse | 1047-TTACTGTTTGAATAGGATATGCCTGTGGAG-1018 |
| Pr-9 (9)  | forward | 5147-TTAAAGGATGAAGAGAAGGGATATTTTCTT-5176 |
| Pr-10 (10) | reverse | 5631-TTTCAATATCATCCCACATAAATCCTGT-5604 |
| Pr-11 (11) | forward | 1-TGGGAAGATTATTGGGATCCTGAAGAAATA-30 |
| Pr-12 (12) | reverse | 5460-CATATCCTATATAATAATC<u>ACGCGT</u>ATGAAAG-CTCCACCT-5421 |
| Pr-13 (13) | forward | 5421-AGGTGGAGCTTTCAT<u>ACGCGT</u>GATTATTATAT-AGGATATG-5460 |
| Pr-14 (14) | reverse | 9464-TGCGAGGTCCCTGGCCCGGACTCC-9441 |
| Pr-16 (15) | reverse | 9444-CTCCAGGGATTCGCAGGTAAGAGAAATTA-9416 |

Combination of the sequences from the 5' and 3' end segments revealed that the LTR of FIV-141 consists of 354 bases, including 208 bases in the U3 region (from nt 1 to 208), 79 bases in the R region (from nt 209–287), and 67 bases in the U5 region (from nt 288 to 354). The terminal 2-base inverted repeat, the TATA box, the polyadenylation signal, and a number of putative cis-acting enhancer-promoter elements were perfectly conserved when compared with other FIV isolates (Talbott et al., 1989, Proc. Natl. Acad. Sci. 86:5743–5747; Miyazawa et al., 1991, J. Virol. 65:1572–1577; Talbott et al., 1990, J. Virol. 64:4605–4613).

6.3. PCR Amplification and Cloning of the Entire Proviral Genome of FIV-141

The sequence information obtained from the three segments described above was used to design FIV-141-specific primers to amplify and clone the entire proviral genome in two pieces, the 5' half and 3' half. Each half was amplified in two rounds of PCR amplification with a semi-nested set of primers. The 5' half of the genome (nts 1 to 5460 of SEQ ID NO:1) was amplified as follows. For the first round PCR amplification, primers Pr-11 (SEQ ID NO:11) and Pr-10 (SEQ ID NO:10) were used (TABLE 1). Briefly, the PCR and Pr-14 (SEQ ID NO:14), were initially used (TABLE 1). The first round PCR amplification was carried out using Pr-9 (SEQ ID NO:9) and Pr-14 (SEQ ID NO:14). Pr-14 (SEQ ID NO:14) is a primer composed of the last 24 bases at the 3' end of the FIV-141 proviral genome. The second round amplification was performed using primers Pr-13 (SEQ ID NO:13) and Pr-14 (SEQ ID NO:14). Pr-13 (SEQ ID NO:13) was overlapped with Pr-12 (SEQ ID NO:12). As with Pr-12 (SEQ ID NO:12), an Mlu I restriction site was incorporated into Pr-13 (SEQ ID NO:13) to facilitate the later construction of the full-length FIV clone. Unfortunately, after two rounds of PCR, no specific DNA band was amplified. Failure to amplify the 3' half genome may have been due to a high GC content and very stable secondary structure in primer Pr-14 (SEQ ID NO:14). Therefore, a new primer, Pr-16 (SEQ ID NO:15), was designed with a sequence ending 20 bases upstream of the last base in the genome. First round PCR amplification was performed using primers Pr-9 (SEQ ID NO:9) and Pr-16 (SEQ ID NO:15), followed by a second round amplification using primers Pr-13 (SEQ ID NO:13) and Pr-16 (SEQ ID NO:15). A DNA fragment of the expected size was obtained after the second round amplification.

The DNA fragments of the 5' half and 3' half of the FIV-141 genome were purified (Wizard PCR Preps DNA purification kit; Promega, Madison, Wis.) and cloned into pCR-Script Amp SK(+) cloning vector (Stratagene, La Jolla, Calif.). Clones from three independent PCR reactions were sequenced for each of the 5' half and 3' half clones. The sequences were obtained by sequencing both strands of the plasmid DNA (Advanced Genetic Analysis Center, St. Paul, Minn.). The authentic consensus sequence for the entire genome of FIV-141 was obtained by combining the sequences of the three independent clones, and is presented herein as SEQ ID NO:1. The DNAStar program (DNAStar Inc., Madison, Wis.) was used to perform sequence assembly, comparison and analysis.

6.4. Cloning of Individual FIV-141 Genes Into pCMV-MCS and pCMV-HA Eukaryotic Expression Vectors The pCMV-MCS expression vector (FIG. 2) was constructed from the pCMVβ reporter vector (Clontech, Palo Alto, Calif.) in the following steps. The β-galactosidase gene was removed from the reporter vector using the Not I restriction sites. A synthetic DNA fragment containing multiple cloning sites (MCS) including a Not I site at both ends, and EcoR V, Avr II, Bgl II, Cla I, Kpn I, Nru I, Pac I, Nhe I, Swa I, Apa I, Sma I, and Spe I sites, was inserted into the backbone pCMVβ vector to generate the expression vector pCMV-MCS. To construct the pCMV-HA expression vector (FIG. 3), a synthetic DNA fragment consisting of a sequence encoding a nine amino acid epitope tag from human influenza hemagglutinin (HA) protein and a translation stop codon immediately following the HA tag was inserted into the pCMV-MCS vector at the Apa I and Spe I sites.

Four FIV genes, including ENV, SU, GAG, and POL, were separately cloned into the pCMV-MCS vector in a similar fashion. Briefly, two primers were designed to amplify the particular gene using either the 5' half or 3' half FIV-141 clones as template (TABLE 2). A Cla I and a Spe I restriction enzyme site were incorporated into the forward and reverse primers, respectively, to facilitate cloning into the vector. The PCR reaction was set up in a volume of 100 μl, consisting of 10×reaction buffer (10 μl), 50 mM MgCl$_2$ (3 μl), 10 mM dNTP (2 μl), each primer (1 μl, 100 ng/μl), template (1 μg/μl), Taq DNA polymerase (0.5 μl, 5 U/μl), and sterile H$_2$O (81.5 μl). PCR amplifications were performed as follows: 94° C. for 3 min; followed by 30 cycles of 94° C. for 30 sec, 55° C. to 62° C. for 1 min, and 72° C. for 2 min. The PCR fragment was purified using a Wizard PCR prep DNA purification kit (Promega, Madison, Wis.), digested with Cla I and Spe I, and then inserted into the pCMV-MCS expression vector that had been digested with these same two restriction enzymes. The entire open reading frame of each gene was verified by sequencing.

For cloning the ENV gene, forward and reverse primers were used, as shown in TABLE 2 below. The Cla I site in the forward primer and the Spe I site in the reverse primer are underlined.

For cloning the SU gene, forward and reverse primers were used, as shown in TABLE 2. The two restriction enzyme sites are underlined. A stop codon (TCA) was incorporated in the reverse primer at nts 23–25.

For cloning the GAG gene, forward and reverse primers were used, as shown in TABLE 2. The Cla I site in the forward primer and the Spe I site in the reverse primer are underlined.

TABLE 2

Primer sequences used to clone FIV genes into eukaryotic expression vectors.[a]

| Expression Vector | Gene | Forward Primer (SEQ ID NO.) | Reverse Primer (SEQ ID NO.) |
|---|---|---|---|
| pCMV-MCS | ENV | 5'-TTTCATCTGC<u>ATCGA</u><u>T</u>AAACATGGCGGAGGGAGG-3'(16) | 5'-CCTGTATTCT<u>ACTAGT</u>CTGAAATGCTCCATCAT-3' (17) |
| pCMV-MCS | SU | 5'-TTTCATCTGC<u>ATCGAT</u>AAACATGGCGGAGGGAGG-3'(18) | 5'-GGGCTAACATAATATG<u>A</u><u>CTAGT</u>TCACCTTTTTTGTTTACCTTTATACCT-3'(19) |
| pCMV-MCS | GAG | 5'-GGTAGG<u>ATCGATTC</u>TACAGCAACATGGGGAATGG-3'(20) | 5'-GTCTTC<u>ACTAGT</u>AAGTTGTGGTAGTACCCATTGTATTATAGT-3'(21) |
| pCMV-MCS | POLI | 5'-GGTAAAA<u>ATCGATCA</u>TGAAACGGGGCGATGGGGCGAGC-3'(22) | 5'-ACTGCA<u>ACTAGT</u>CTTCTACTTACCTGCCAATCTTCG-3'(23) |
| pCMV-MCS | POLII | 5'-TGTTAG<u>ATCGATAAT</u>GTATAATAAAGTGGGTACCACC-3'(24) | 5'-ACTGCA<u>ACTAGT</u>CTTCTACTTACCTGCCAATCTTCG-3'(25) |
| pCMV-HA | MA | 5'-GGTAGG<u>ATCGATTCT</u>ACAGCAACATGGGGAATGG-3'(26) | 5'-CTGTTT<u>GGGGCCCAT</u>AAGCCTGTGGAGGTCCTTCTTC-3'(27) |
| pCMV-HA | CA | 5'-GGACCT<u>ATCGAT</u>ACCATGCCTATTCAAACAGTAAATGGAGCACC-3'(28) | 5'-TGCTTG<u>GGGCCC</u>TTGCACCCTAGTAAGAGCCTCTGC-3'(29) |
| pCMV-HA | NC | 5'-GGCTCTT<u>ATCGAT</u>ACCATGACAGTTCAAGCAAAGGACCAAG-3'(30) | 5'-TATTAT<u>GGGCCC</u>ATATCTAACAATTTCTCCTCTACCG-3'(31) |
| pCMV-HA | Vif | 5'-CCCTGCACTCTTC<u>AT</u><u>CGAT</u>ACCATGAGTGACGAAGATTGGCAGG-3'(32) | 5'-GGGATTATTTCTT<u>CGG</u><u>GCCCT</u>AATTCTCCTGTCCACAATAAATTCCT-3'(33) |
| pCMV-HA | ORF-2 | 5'-TTGTGGACGGGA<u>ATC</u><u>GAT</u>ACCATGGAAGAAATAATCCCACTG-3'(34) | 5'-ATATTAAAAGAAATA<u>GG</u><u>GCCC</u>GGCAGTATTTATGGATAATGT-3'(35) |
| pCMV-HA | TM | 5'-GTATAAAGGT<u>ATCGA</u><u>T</u>ACCATGGCCGCTATTCATATTATGTTAGCC-3' (36) | 5'-TGAAATGC<u>TGGGCCCT</u>TCCTCCTCTTTTTCAGATATGCCACA-3'(37) |

TABLE 2-continued

Primer sequences used to clone FIV genes into eukaryotic expression vectors.[a]

| Expression Vector | Gene | Forward Primer (SEQ ID NO.) | Reverse Primer (SEQ ID NO.) |
|---|---|---|---|
| pCMV-HA | Rev | 5'-TTTCATCTGC<u>ATCG AT</u>AAACATGGCGGAGG GAGG-3'(38) | 5'-TGTACG<u>GGGCCC</u>GTCC ATTAGCATTTTTTCTATTT C-3'(39) |
| pCMV-HA | PR | 5'-TGTTAG<u>ATCGAT</u>AATG TATAATAAAGTGGGTAC CACC-3'(40) | 5'-CTCTGAAAC<u>GGGCCCC</u> ATTACCAACCTTATGTTGA ACTTAATC-3'(41) |
| pCMV-HA | RT | 5'-AACATA<u>ATCGAT</u>ACCA TGGTCCAGATTTCAGAG AAAATTCCAATAG-3'(42) | 5'-TTCTAG<u>GGGCCCC</u>ATC GTTTGACAAAGTTCATCTA CCTC-3'(43) |
| pCMV-HA | DU | 5'-CTTTGT<u>ATCGAT</u>ACCA TGGTTATAGAAGGTGAA GGAATATTAG-3'(44) | 5'-CACCC<u>AGGGCCC</u>AAAG ACTCCAGTTGACCCAAAT CCC-3'(45) |
| pCMV-HA | IN | 5'-GGGTCA<u>ATCGAT</u>ACA ATGTCTTCATGGGTGGA CAGAATTGAA-3'(46) | 5'-CAATCT<u>GGGCCC</u>CTCA TCACCTTCAGGAAGAGTG CAGG-3'(47) |

[a]Cla I and Spe I (or Apa I) restriction sites are underlined in forward and reverse primers, respectively.

For cloning the POL gene into the vector, two expression constructs (POL I and POL II) were made. The N-terminus of the POL I construct begins with the first residue of the shifted POL open reading frame, while the N-terminus of the POL II construct begins at the first residue of the protease (PR) protein. An initiation (ATG) codon with Kozak context was introduced immediately upstream of the POL gene for both POL I and POL II constructs. For cloning POL I, forward and reverse primers were used as shown in TABLE 2. The two restriction sites are underlined, and the introduced ATG initiation codon in the forward primer is at primer nts 15–17. For cloning POL II, forward and reverse primers were used as shown in TABLE 2. The two restriction sites are underlined, and the introduced ATG initiation codon in the forward primer is at primer nts 14–16.

Eleven FIV-141 genes, including matrix (MA), capsid (CA), nucleocapsid (NC), protease (PR), reverse transcriptase (RT), deoxyuridine triphosphatase (DU), integrase (IN), transmembrane (TM), Vif, ORF2 and Rev, were each separately cloned into the expression vector, pCMV-HA. All the clones, except for Rev, were made in a similar fashion. Each individual gene was amplified using either the 5' half or 3' half clone of FIV-141 as template, and a set of primers as shown in TABLE 2, with the same amplification conditions as above. Cla I and Apa I restriction sites were incorporated into forward and reverse primers, respectively. After being digested with Cla I and Apa I, each gene fragment was cloned into the pCMV-HA expression vector that had been digested with these same two restriction enzymes. To clone the Rev gene, total mRNA extracted from FIV-141-infected peripheral blood mononuclear cells (PBMCs) was reverse transcribed into cDNA, followed by PCR amplification. For each clone, the entire open reading frame of each gene was verified by sequencing.

For cloning MA, forward and reverse primers were used as shown in TABLE 2. The introduced Cla I and Apa I sites are underlined in the forward and reverse primer, respectively.

For cloning CA, forward and reverse primers were used as shown in TABLE 2. An initiation codon (ATG) was incorporated into the forward primer immediately upstream of the coding region of the CA gene, as shown in TABLE 2 at primer nts 16–18. The introduced Cla I and Apa I sites in the forward and reverse primers, respectively, are underlined.

For cloning NC, forward and reverse primers were used as shown in TABLE 2. An initiation codon (ATG) was incorporated into the forward primer immediately upstream of the coding region of the NC gene, as shown in TABLE 2 at primer nts 17–19. The introduced Cla I and Apa I sites in the forward and reverse primers, respectively, are underlined.

For cloning Vif, forward and reverse primers were used as shown in TABLE 2. The introduced Cla I and Apa I sites in the forward and reverse primers, respectively, are underlined.

For cloning ORF2, forward and reverse primers were used as shown in TABLE 2. The introduced Cla I and Apa I sites in the forward and reverse primers, respectively, are underlined.

For cloning Rev, forward and reverse primers were used as shown in TABLE 2. The ATG initiation codon in the primer at nts 21–23 is the authentic ATG codon from Rev. The introduced Cla I and Apa I sites in the forward and reverse primer, respectively, are underlined.

For cloning TM, forward and reverse primers were used as shown in TABLE 2. An initiation codon (ATG) was incorporated in the forward primer immediately upstream of the coding region of the TM gene, as shown in TABLE 2 at primer nts 20–22. The introduced Cla I and Apa I sites in the forward and reverse primer, respectively, are underlined.

For cloning PR, forward and reverse primers were used as shown in TABLE 2. An initiation codon (ATG) was incorporated in the forward primer immediately upstream of the coding region of the PR gene, as shown in TABLE 2 at primer nts 14–16. The introduced Cla I and Apa I sites in the forward and reverse primers, respectively, are underlined.

For cloning RT, forward and reverse primers were used as shown in TABLE 2. An initiation codon (ATG) was incorporated in the forward primer immediately upstream of the coding region of the RT gene, as shown in TABLE 2 at primer nts 16–18. The introduced Cla I and Apa I sites in the forward and reverse primers, respectively, are underlined.

For cloning DU, forward and reverse primers were used as shown in TABLE 2. An initiation codon (ATG) was incorporated in the forward primer immediately upstream of the coding region of the DU gene, as shown in TABLE 2 at primer nts 16–18. The introduced Cla I and Apa I sites in the forward and reverse primers, respectively, are underlined.

For cloning IN, forward and reverse primers were used as shown in TABLE 2. An initiation codon (ATG) was incorporated in the forward primer immediately upstream of the coding region of the IN gene, as shown in TABLE 2 at primer nts 16–18. The introduced Cla I and Apa I sites in the forward and reverse primers, respectively, are underlined.

7. EXAMPLE

IN VITRO EXPRESSION OF FIV GENES

7.1. Transfection of FIV Gene Constructs

Plasmid DNAs from each of the FIV gene constructs prepared as described above were separately transfected (2 µg/well) into Crandell feline kidney (CRFK) cells that were 40–60% confluent in a 6-well plate, using Trans IT Polyamine Transfection Reagents (Mirus, Madison, Wis.) according to the manufacturer's protocol. Briefly, Trans IT Lt-1 (PANVERA) (10 µl) was mixed with RPMI 1640 medium (1 ml) and incubated at room temperature for 15 min. Plasmid DNA (2 µg) was added to the RPMI/Lt-1 solution, and incubated at room temperature for another 15 min. Old culture medium was removed from the cell monolayer, and the cells were washed once with serum-free RPMI. The cells were then incubated in the DNA cocktail in a $CO_2$ incubator (5% $CO_2$) at 37° C. for 4 hr. The DNA cocktail was removed, and 2 ml of fresh RPMI 1640 medium with 3% fetal calf serum (FCS) was added to each well. Transfected cells were analyzed 48 hr later for protein expression by Western blot, RT-PCR, and functional RT activity assays.

7.2. FIV-141 Gene Expression Detected by Western Blot Analysis

Transfected CRFK cells prepared as described above were harvested at 48 hr and lysed with 2×SDS-PAGE loading buffer. Cell lysates were loaded and run on a 4–20% gradient SDS-PAGE gel, followed by protein transfer onto polyvinylidene difluoride (PVDF) membranes (0.22 µM, BIO-RAD, Hercules, Calif.). The primary antibody, anti-HA MAb specific to the HA tag (Boehringer Mannheim, Indianapolis, Ind.), or serum from FIV infected cats, was applied to the appropriate blot and incubated for 3 hr. After washing, antibody binding to specific proteins was detected with an alkaline phosphate-conjugated secondary antibody, as recommended by the manufacturer (Boehringer Mannheim, Indianapolis, Ind.).

A specific protein band of the appropriate size was detected by Western blot for eleven expression clones, including the GAG polyprotein, MA, CA, NC, PR, DU, IN, Vif, Rev, ORF2 and TM, indicating that transfected cells carrying these constructs expressed the corresponding FIV gene products.

7.3. FIV-141 Gene Expression Detected by RT-PCR

Seven expression constructs, including PR, DU, ENV, SU, Vif, POL I and POL II, were assayed by RT-PCR. Total RNA was harvested from transfected CRFK cells at 48 hr by lysing with a tissue shredder (Qiagen, Chatsworth, Calif.), followed by purification (RNA purification kit; Qiagen). RNA was eluted in DEPC-treated $H_2O$ (50 µl). cDNA was made with random hexamers as primers and SuperScript II reverse transcriptase (Gibco BRL, Gaithersburg, Md.). Duplicate reactions were set up in the presence or absence of SuperScript II RT. FIV specific oligonucleotides were used to amplify gene specific fragments by PCR. PCR products were analyzed by running each sample (10 µl) on a 1.2% agarose gel.

The RT-PCR data indicated that cells transiently transfected with each of the seven constructs expressed the appropriate mRNA.

7.4. FIV-141 Gene Expression Detected by Reverse Transcriptase (RT) Activity Assay Gene expression of the RT, POL I and POL II constructs was tested by RT activity assay using a Reverse Transcription Assay Kit (Boehringer Mannheim). Transfected CRFK cells were harvested at 48 hr post-transfection, and resuspended in lysis buffer (40 µl). The RT ELISA assay was performed according to the manufacturer's protocol (Boehringer Mannheim, Indianapolis, Ind.). The results showed that the RT construct, but not the POL I and POL II constructs, resulted in significant RT activity, indicating that functional RT protein was expressed in transfected cells carrying the RT construct. Failure to detect RT activity for the POL I and POL II constructs may indicate that the expressed protein was not properly processed.

8. EXAMPLE

EFFICACY OF DNA VACCINATION IN CATS

8.1. Preparation of Plasmid DNA for Vaccination

Production of bulk purified plasmid DNA for this animal study was contracted to Bayou Biolabs (Harahan, La.). Coded samples of plasmid DNA (1 µg) were sent and each was transformed into DH5α E. coli competent cells. Each clone was grown in 8 liters of enriched broth. Plasmid DNA in all forms was purified first, followed by purification of the supercoiled form. The final purified DNA was dissolved in phosphate buffered saline (PBS) with 1 mM EDTA at a concentration of 2–5 µg/µl. DNA concentration was determined by UV absorbance and by fluorometry. Both methods gave the same concentration, confirming an absence of nucleotide contamination. Plasmid DNA was also analyzed by electrophoresis on a 1% agarose gel. Ethidium bromide stained gels showed that all the supercoiled purified plasmid DNA preparations were a mixture of mostly supercoiled plasmid with a small amount of dimeric supercoiled plasmid. No linear or nicked plasmid DNA, chromosomal DNA or mRNA contamination was visible on the gel. The plasmid DNA was shipped on dry ice and stored at –70° C.

8.2. Vaccination and Challenge

Four experimental vaccines were assembled, each with different combinations of the 16 FIV-141 gene constructs (300 µg DNA from each construct/dose). Vaccine 1 (XFIV-1) consisted of all 16 FIV-141 gene constructs. Vaccine 2 (XFIV-2) consisted of 7 structural gene constructs, including GAG, MA, CA, NC, ENV, SU and TM. Vaccine 3 (XFIV-3) consisted of a mixture of structural and nonstructural gene constructs, including DU, PR, GAG, NC and MA. Vaccine 4 (XFIV-4) consisted of 9 nonstructural and regulatory gene constructs, including Rev, ORF2, Vif, IN, DU, RT, PR, POL I and POL II.

Placebo consisted of both pCMV-MCS and pCMV-HA expression vectors in equal proportions. Since the total DNA given in one dose varied between experimental vaccines, the amount of placebo DNA (2400 µg) was an average between the highest and lowest DNA doses. The appropriate volume of stock DNA from each construct was dissolved in sterile PBS (GIBCO). The final volume for each dose ranged from 2–3 ml.

Antibody-profile defined, barrier-reared, domestic cats (n=60, approximately 8 weeks of age, no smaller than 0.5 kg) were obtained from Liberty Research, Inc. (Waverly, N.Y.). Cats were vaccinated with killed vaccines to feline herpes virus, feline calicivirus, and feline parvovirus. Sixty cats were randomly assigned by litter and sex to 6 groups prior to vaccination (TABLE 3).

TABLE 3

| GROUP | VACCINE | CHALLENGE | n |
|---|---|---|---|
| 1 | Placebo | YES | 10 |
| 2 | Placebo | NO | 10 |
| 3 | XFIV-1 | YES | 10 |
| 4 | XFIV-2 | YES | 10 |
| 5 | XFIV-3 | YES | 10 |
| 6 | XFIV-4 | YES | 10 |

Combinations and doses of FIV-141 gene constructs in experimental vaccines are detailed in TABLE 4.

TABLE 4

| VACCINE | ANTIGEN(S)-QUANTITY/DOSE | VOL/ DOSE |
|---|---|---|
| Placebo | 1200 µg pCMV-MCS DNA + 1200 µg pCMV-HA DNA; Total = 2400 µg DNA | 2 ml |
| XFIV-1 | 300 µg each DNA from Gag, POL I, POL II, ENV, SU, TM, PR, RT, DU, IN, Ma, CA, NC, Vif, Rev, ORF2; Total = 4800 µg DNA | 3 ml |
| XFIV-2 | 300 µg each from Gag, TM, SU, ENV, NC, CA, MA; Total = 2100 µg DNA | 2 ml |
| XFIV-3 | 300 µg each of DU, PR, NC, Gag, MA; Total = 1500 µg DNA | 2 ml |
| XFIV-4 | 300 µg each of Rev, ORF2, Vif, IN, DU, RT, PR, POL I, POL II; Total = 2700 µg | 2 ml |

Vaccine were administered intramuscularly at 4 week intervals when cats were 8, 12 and 16 weeks of age. Four weeks following the last vaccination, cats were challenged at age 20 weeks by inoculating 354 TCID$_{50}$ FIV-141 virus subcutaneously in the nape of the neck, and total of 8 weeks post-challenge.

8.3. Evaluation of Vaccine Efficacy

Similar to HIV-1 disease progression (Graziosi et al., 1993, Proc. Natl. Acad. Sci. 90:6406–6409), FIV RNA load in plasma has been demonstrated to correlate with disease stage, and can predict disease progression in accelerated FIV infection (Diehl et al., 1995, J. Virol. 69:2328–2332; Diehl et al., 1996, J. Virol. 70:2503–2507). In this study, peripheral blood was drawn weekly to monitor the efficacy of the vaccination. Plasma viral loads were determined by both quantitative competitive-reverse transcription-polymerase chain reaction (QcRT-PCR), and quantitative virus isolation on FeP2 cell culture.

8.3.1. Quantitation of Viral RNA in Plasma by QcRT-PCR

Viral RNA was isolated from plasma samples using QIAmp Viral RNA Purification Kit (Qiagen). Each purified RNA sample was distributed into four tubes, and into each tube was added an internal competitive RNA template with decreasing amounts of RNA (from 1000 fg, 100 fg, 10 fg to 1 fg). RNA samples were subjected to RT-PCR using the Titan One Tube RT-PCR System (Boehringer Mannheim). A one-step PCR protocol provided by the manufacturer was performed with minor modifications to increase the sensitivity of the assay. The RT-PCR reaction was set up in a total volume of 38.5 µl containing: 6.5 mM DTT, 0.3 units RNase inhibitor, 0.3 mM dATP, 0.3 mM dGTP, 0.3 mM dTTP, 0.3 mM dCTP, 10.4 ng of each FIV specific oligonucleotide, i.e., QPCR-11 (forward primer 1392-TGTAGAGCATGGTAT CTTGAAGCATTAGGAAA-1423) (SEQ ID NO. 48), and QPCR-O2 (reverse primer 2175-GTTCCTCTCTTTCCGCCTCCTACTCCAATCATATT-2141) (SEQ ID NO:49), 1.95 mM MgCl$_2$, and 1 µl of Titan Enzyme Mix. RT-PCR amplification conditions were 50° C. for 90 min, 94° C. for 3 min; followed by 30 cycles of denaturing at 94° C. for 30 sec, annealing at 55° C. for 1 min, and extension at 72° C. for 2 min; followed by 72° C. for 10 min.

Each PCR sample was separated on a 1.0% agarose gel and stained with ethidium bromide. Quantitation of viral RNA load was determined by comparing the intensity of the positive DNA band with that of the internal competitive standard control DNA band using the Gel-Doc system (Bio-Rad Laboratories).

8.3.2. Quantitation of Viral Load in Plasma by Virus Isolation

Virus quantitation by culture was performed based on a modification of a method described by Meers et al., 1992, Arch. Virol. 127:233–243. An IL-2 dependent feline T cell line (FeP2 cells) developed in the laboratory was used for virus isolation from plasma. FeP2 cells were grown in complete medium (CM) consisting of RPMI 1640 supplemented with 10% heat-inactivated fetal bovine serum (FBS), 1% GlutaMAX-1, Insulin-Transferrin-Selenium-S (ITS-S) 43 mg/ml (100x) at 1%, Non-Essential Amino Acids Solution (NEAA) 10 mM (100x) at 1%, 2-mercaptoethanol 5.5×10$^{-2}$ M (1000x) at 1 µl/ml, sodium pyruvate 100 mM (100x) at 1%, gentamicin 50 mg/ml at 0.1%, recombinant human IL-2 at 100 U/ml, and Con A at 1 µg/ml. Each plasma sample was diluted 10-fold (10$^{-1}$ to 10$^{-4}$) in a 48-well plate using diluent media (DM) consisting of RPMI-1640 supplemented with 5% FBS, 20 mM HEPES, 50 µg/ml gentamicin, 4U/ml heparin. Infection was carried out by adding 8.5×10$^5$ of FeP2 cells into each well, followed by incubating at 37° C. for 0.5 to 2 hr. CM (700 µl) was then added to each well and cultures were maintained in the following manner: at day 3, 500 µl of supernatant was removed from each well and 700 µl of CM was added back; at days 7, 10, 13, 16, 19, 22 and 25, 675 µl of supernatant was removed from each well and 700 µl of CM was added back. Cultures were terminated at day 30. From day 19 to 30, the culture fluid removed from each well was tested for the presence of FIV p26 using an FIV p26 antigen kit (IDEXX). Virus titer was calculated as the reciprocal of the last positive dilution and reported as tissue culture infectious dose (TCID)$_{100}$/mL.

8.3.3. Viral Load in Plasma Post-challenge

Compared with group 1 (placebo, challenged), groups 4 and 5 exhibited significant decreases in cumulative plasma viral load during the period of 8 weeks post-challenge. Groups 4 and 5 exhibited decreases of 19.3 fold and 25.4 fold, respectively, in cumulative plasma viral loads, as determined by virus isolation (FIG. 4). Groups 4 and 5 also exhibited decreases of 7.0 and 7.1 fold, respectively, in cumulative plasma viral RNA loads, as detected by QcRT-PCR (FIG. 5). Group 4 was vaccinated with XFIV-2 consisting of 7 structural gene constructs, including GAG, MA, CA, NC, ENV, SU and TM. Group 5 was vaccinated with XFIV-3 consisting of a mixture of structural and nonstructural gene constructs, including GAG, NC, MA, DU and PR. Group 3 exhibited a 4.4 fold decrease in plasma viral load, as determined by virus isolation, and a decrease of 6.7 fold in plasma viral RNA load, as determined by QcRT-PCR (FIGS. 4, 5). Group 3 was vaccinated with XFIV-1 consisting of all 16 gene constructs. Group 6 exhibited a 3.8 fold decrease in plasma viral load and plasma viral RNA load, as determined by virus isolation and QcRT-PCR, respectively (FIGS. 4, 5). Group 6 was vaccinated with XFIV-4 consisting of 9 nonstructural and regulatory gene constructs, including Rev, ORF2, Vif, IN, DU, RT, PR, POL I and POL II.

Compared with group 1 (placebo, challenged), group 5 exhibited fewer time points when plasma virus titers were higher than 10 infectious doses/ml, as detected by virus isolation (FIG. 6). Throughout the 8 week study, only 3 cats, for a total of 4 time points, were determined to have virus titers higher than 10 infectious doses/ml. Consistent with this observation is the decreased number of total positive time points in group 5, as detected by QcRT-PCR (FIG. 7). Viral RNA in plasma was detected at 10 time points throughout the whole study for group 5. Following group 5 is group 4, which had a marked decrease in the number of positive time points at which virus titers were higher than 10 infectious doses/ml, as detected by virus isolation. Moderately fewer positive time points, compared to control, for plasma viral RNA were detected in group 4 by QcRT-PCR throughout the whole study (FIGS. 6 and 7). A slight decrease in positive time points for both virus isolation and QcRT-PCR was observed in group 3 compared with positive control (FIGS. 6 and 7). There appears to be no difference between group 6 and group 1 in terms of the number of positive time points detected by both virus isolation and QcRT-PCR (FIGS. 6 and 7).

Although no vaccinated group tested in this study was totally protected from infection (i.e., sterilizing immunity), decreases in plasma viral load were demonstrated in groups 4 and 5 during the monitoring period of 8 weeks post-challenge. FIV antigens in common among the two groups as encoded by the vaccine DNA include the GAG polyprotein, MA and NC proteins. Among the various conclusions of this study, we conclude that the GAG polyprotein and its substituent proteins, MA, CA and NC can stimulate protective immunity against FIV infection, and that polynucleotide molecules encoding these proteins are useful as vaccine agents.

All patents, patent applications, and publications cited above are incorporated herein by reference in their entirety.

The present invention is not limited in scope by the specific embodiments described, which are intended as single illustrations of individual aspects of the invention. Functionally equivalent compositions and methods are within the scope of the invention. Indeed, various modifications of the invention, in addition to those shown and described herein, will become apparent to those skilled in the art from the foregoing description. Such modifications are intended to fall within the scope of the appended claims.

What is claimed is:

1. A vaccine composition against feline immunodeficiency virus (FIV) comprising an immunologically effective amount of polynucleotide molecules including nucleotide sequences or degenerate variants thereof encoding at least two different GAG proteins from FIV; and a veterinarily acceptable carrier, wherein said nucleotide sequences do not replicate in a feline host cell.

2. A vaccine composition against feline immunodeficiency virus (FIV) comprising an immunologically effective amount of polynucleotide molecules including nucleotide sequences or degenerate variants thereof encoding a combination of FIV proteins that are on two or more different polynucleotide molecules; and a veterinarily acceptable carrier, wherein said nucleotide sequences do not replicate in a feline host cell.

* * * * *